(12) United States Patent
Cushen et al.

(10) Patent No.: US 12,558,108 B2
(45) Date of Patent: Feb. 24, 2026

(54) SLEEVE FOR ROTARY SURGICAL INSTRUMENT

(71) Applicant: Stryker European Operations Limited, Carrigtwohill (IE)

(72) Inventors: Patrick Cushen, Cork (IE); Eoin Connolly, Dublin (IE)

(73) Assignee: Stryker Corporation, Portage, MI (US)

( * ) Notice: Subject to any disclaimer, the term of this patent is extended or adjusted under 35 U.S.C. 154(b) by 1025 days.

(21) Appl. No.: 17/640,982

(22) PCT Filed: Sep. 3, 2020

(86) PCT No.: PCT/IB2020/058223
§ 371 (c)(1),
(2) Date: Mar. 7, 2022

(87) PCT Pub. No.: WO2021/044347
PCT Pub. Date: Mar. 11, 2021

(65) Prior Publication Data
US 2022/0330951 A1      Oct. 20, 2022

Related U.S. Application Data

(60) Provisional application No. 62/896,056, filed on Sep. 5, 2019.

(51) Int. Cl.
*A61B 17/16*          (2006.01)

(52) U.S. Cl.
CPC ...... *A61B 17/1644* (2013.01); *A61B 17/1633* (2013.01); *A61B 2217/007* (2013.01)

(58) Field of Classification Search
CPC ............ A61B 17/1644; A61B 17/1633; A61B 2217/007
See application file for complete search history.

(56) References Cited

U.S. PATENT DOCUMENTS 5,709,698 A      1/1998  Adams et al.
5,989,183 A     11/1999  Reisdorf et al.
(Continued)

FOREIGN PATENT DOCUMENTS

DE      202005018372 U1      1/2006
EP          0791336 A1      8/1997
(Continued)

OTHER PUBLICATIONS

English language abstract and machine-assisted English translation for DE 20 2005 018 372 U1 extracted from espacenet.com database on Apr. 26, 2024, 10 pages.
(Continued)

*Primary Examiner* — Kevin T Truong
*Assistant Examiner* — Diana Jones
(74) *Attorney, Agent, or Firm* — Howard & Howard Attorneys PLLC

(57)                ABSTRACT

An instrument sleeve is provided for use with a surgical rotary instrument having a tube extending to a distal tube end, and a cutting accessory having a head and a shank extending from the head adapted to be rotatably supported by the tube of the rotary instrument. The instrument sleeve comprises a sleeve body extending between proximal and distal sleeve portions, a first lumen for receiving at least a portion of the tube of the rotary instrument, and a shield extension coupled to the sleeve body. The shield extension extends between proximal and distal shield portions the proximal shield portion engaged with the distal sleeve portion and adapted to minimize tissue wrap about the cutting accessory shank.

17 Claims, 16 Drawing Sheets

(56)  References Cited

U.S. PATENT DOCUMENTS

| | | | | |
|---|---|---|---|---|
| 6,110,103 | A | 8/2000 | Donofrio | |
| 6,669,710 | B2 | 12/2003 | Moutafis et al. | |
| 7,811,228 | B2 | 10/2010 | Adams | |
| 7,837,687 | B2 * | 11/2010 | Harp .................. | A61B 17/1659 |
| | | | | 606/85 |
| 10,881,425 | B2 * | 1/2021 | Tanigami ....... | A61B 17/320068 |
| 2001/0018584 | A1 | 8/2001 | Bays | |
| 2006/0030797 | A1 | 2/2006 | Zhou et al. | |
| 2012/0221034 | A1 | 8/2012 | Dinger, III et al. | |
| 2015/0119915 | A1 | 4/2015 | Neurohr et al. | |
| 2015/0223855 | A1 * | 8/2015 | Nardini .................. | A61B 17/68 |
| | | | | 606/323 |
| 2017/0042528 | A1 * | 2/2017 | Ellegala ......... | A61B 17/320092 |
| 2017/0095265 | A1 | 4/2017 | Ahluwalia et al. | |

FOREIGN PATENT DOCUMENTS

| | | | |
|---|---|---|---|
| JP | 2003520078 | A | 7/2003 |
| WO | 2019022791 | A1 | 1/2019 |

OTHER PUBLICATIONS

English language abstract for JP 2003-520078 A extracted from espacenet.com database on Apr. 26, 2024, 2 pages.
Partial International Search Report for Application No. PCT/IB2020/058223 dated Nov. 26, 2020, 3 pages.
International Search Report for Application No. PCT/IB2020/058223 dated Feb. 4, 2021, 3 pages.

* cited by examiner

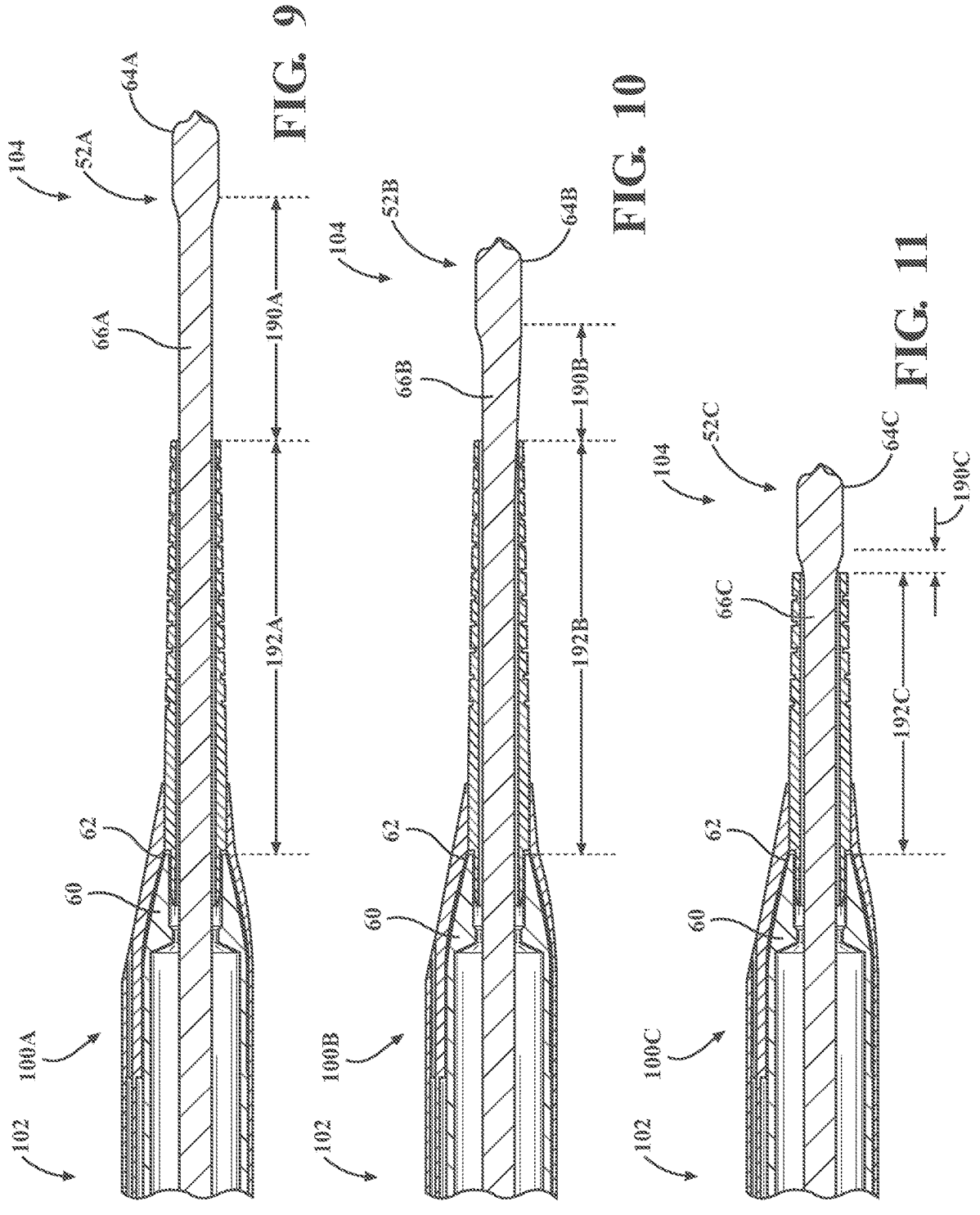

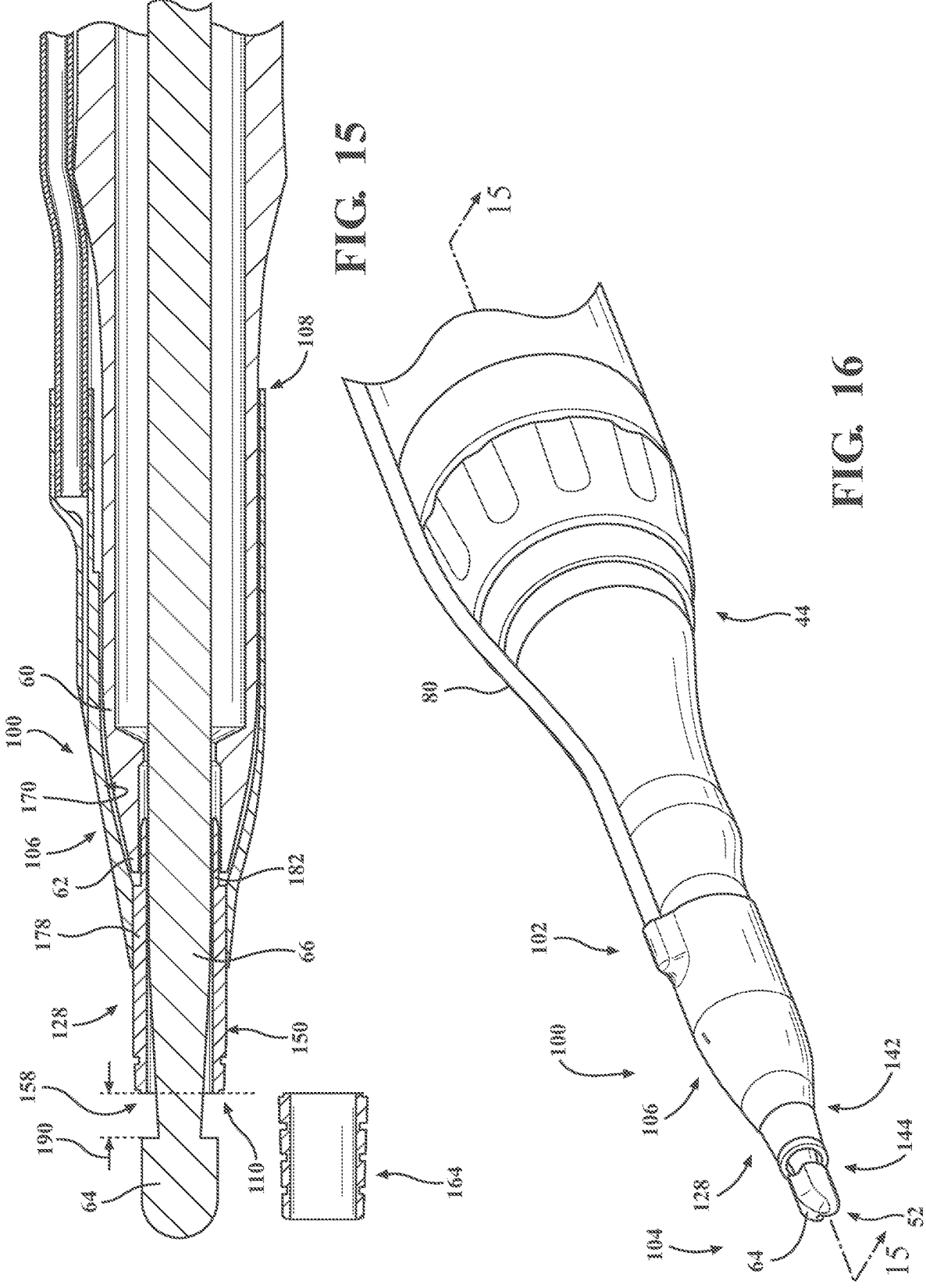

SLEEVE FOR ROTARY SURGICAL INSTRUMENT

CROSS-REFERENCE TO RELATED APPLICATIONS

The subject patent application is a National Stage of International Patent Application No. PCT/IB2020/058223, filed on 3 Sep. 2020, which claims priority to and all the benefits of U.S. Provisional Patent application Ser. No. 62/896,056, filed on 5 Sep. 2019, the entire contents of which are hereby incorporated by reference.

BACKGROUND

Conventional medical procedures routinely involve the use of surgical tools to assist medical professionals in approaching, viewing, manipulating, or otherwise effecting treatment at localized surgical sites. Some of these medical procedures may involve surgical techniques such as drilling, shaping, or decortication of bone using a rotary instrument, where a cutting accessory, such as a high-speed bur, rotates at speeds in excess of 75k rpm to remove tissue. During use, contact between non-cutting portions of the bur (e.g., a shank) and soft tissue can result in tissue wrap, in which friction between the rotating shank and the soft tissue causes the soft tissue to be pulled around the shank. Surgeons must be mindful to avoid unexpected tissue wrap.

SUMMARY

An irrigation sleeve for use with a surgical system comprising an irrigation source, a rotary instrument having a tube extending to a distal tube end, and a cutting accessory having a head and a shank adapted to be rotatably supported by the tube of the rotary instrument, the irrigation sleeve including a sleeve body extending between a proximal sleeve portion and a distal sleeve portion; a first lumen formed in the sleeve body for receiving at least a portion of the tube of the rotary instrument; a second lumen formed in the sleeve body and spaced out of fluid communication with the first lumen; a shield extension coupled to the sleeve body and extending between a proximal shield portion and a distal shield portion, the proximal shield portion engaged with the distal sleeve portion, the shield extension adapted to minimize tissue wrap about the cutting accessory shank; and a third lumen formed in the shield extension and in communication with the first lumen.

An irrigation sleeve for use with a surgical system including an irrigation source, a rotary instrument having a tube extending to a distal tube end, and a cutting accessory adapted to be rotatably supported by the tube of the rotary instrument, the irrigation sleeve including a sleeve body extending between a proximal sleeve end and a distal sleeve end and having an outer surface; a first lumen formed in the sleeve body for receiving at least a portion of the tube of the rotary instrument; a second lumen formed in the sleeve body and spaced out of fluid communication with the first lumen for being coupled to the irrigation source; a length indicia arranged on the outer surface of the sleeve body and spaced a predetermined distance from the proximal sleeve end for indicating a distance between the length indicia and the proximal sleeve end; and a pilot member coupled to the sleeve body and extending partially into the first lumen and defining a third lumen in communication with the first lumen, wherein the pilot member extends in a proximal direction to engage a portion of the distal tube end to provide rigidity of the sleeve body.

An irrigation sleeve for use with a surgical system including an irrigation source, a rotary instrument having a tube extending to a distal tube end, and a cutting accessory adapted to be rotatably supported by the tube of the rotary instrument, the irrigation sleeve including a sleeve body having a proximal portion and a distal portion, the proximal portion defining a first lumen for receiving at least a portion of the tube of the rotary instrument; a second lumen formed in the proximal sleeve body and spaced out of fluid communication with the first lumen; and wherein the distal portion protrudes from the proximal portion and comprises a plurality of weakened segments, the weakened segments arranged along the distal portion at predetermined intervals for facilitating customization of a length of the sleeve body.

An instrument sleeve for use with a rotary instrument having a tube extending to a distal tube end, and a cutting accessory having a head and a shank extending from the head, the instrument sleeve including a sleeve body extending between a proximal sleeve end and a distal sleeve end and having an outer surface; a first lumen formed by an inner surface of the sleeve body for receiving at least a portion of the tube of the rotary instrument, the inner surface extending between the proximal sleeve end and a first lumen apex; and a pilot member arranged in the first lumen for engaging the distal tube end, the pilot member having an outer surface extending between a proximal pilot end and the first lumen apex.

A method for customizing a surgical system including a rotary instrument having a tube extending to a distal tube end, and a cutting accessory adapted to be rotatably supported by the tube of the rotary instrument, the method including providing an irrigation sleeve having a sleeve body, a lumen formed in the sleeve body, and a shield extension having at least one length indicia coupled to the sleeve body; severing the shield extension at one of the at least one length indicia; coupling the irrigation sleeve to the rotary instrument such that at least a portion of the tube is disposed in the lumen.

A method for customizing a surgical system including a rotary instrument having a tube extending to a distal tube end, and a cutting accessory having a head and a shank extending from the head adapted to be rotatably supported by the tube of the rotary instrument, the method including providing an irrigation sleeve including a sleeve body having a plurality of weakened segments, a lumen formed in the sleeve body, and a pilot member disposed in the first lumen; sliding the sleeve body over the rotary instrument such that the tube is received by the lumen; engaging the pilot member with the distal tube end; removing at least one of the weakened segments from the sleeve body such that when the cutting accessory is rotatably supported by the tube of the rotary instrument the shank engages the rotary instrument and the head is spaced from the lumen; and inserting the cutting accessory into the lumen and engaging the shank with the rotary instrument.

BRIEF DESCRIPTION OF THE DRAWINGS

Advantages of the present disclosure will be readily appreciated as the same becomes better understood by reference to the following detailed description when considered in connection with the accompanying drawings.

FIG. 9 is a partial section view through a vertical plane on line 8-8 in FIG. 7 showing the irrigation sleeve and the rotary instrument tube according to another embodiment, shown with a first alternative cutting accessory.

FIG. 10 is a partial section view through a vertical plane on line 8-8 of FIG. 7 showing the irrigation sleeve and the rotary instrument tube of FIG. 9, shown with a second alternative cutting accessory.

FIG. 11 is a partial section view through a vertical plane on line 8-8 of FIG. 7 showing the irrigation sleeve and the rotary instrument tube of FIG. 9, shown with a portion of the irrigation sleeve removed and a third alternative cutting accessory.

FIG. 15 is a partial section view through a vertical plane on line 15-15 of FIG. 16 showing the rotary instrument and the irrigation sleeve of FIGS. 12-14, shown with the cutting accessory installed in the rotary instrument and showing the removed distal portion of the irrigation sleeve.

FIG. 16 is a partial perspective view of the rotary instrument, the cutting accessory, and the irrigation sleeve of FIGS. 12-15.

DETAILED DESCRIPTION

Figure 1:
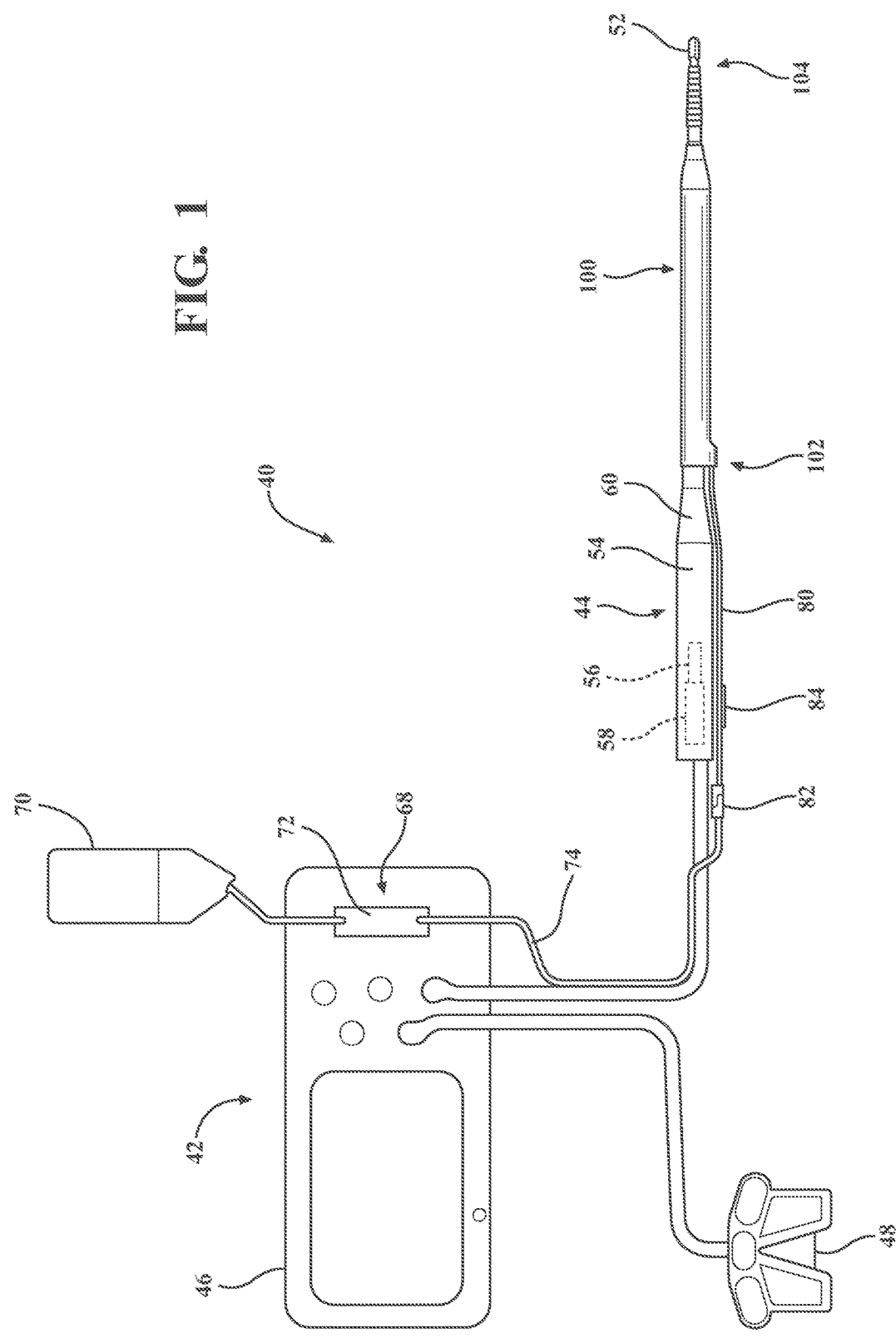
FIG. 1 is a schematic view of a surgical system comprising a console, an irrigation source, and a rotary instrument with a cutting accessory, shown with an irrigation sleeve coupled to the rotary instrument.
Figure 2:
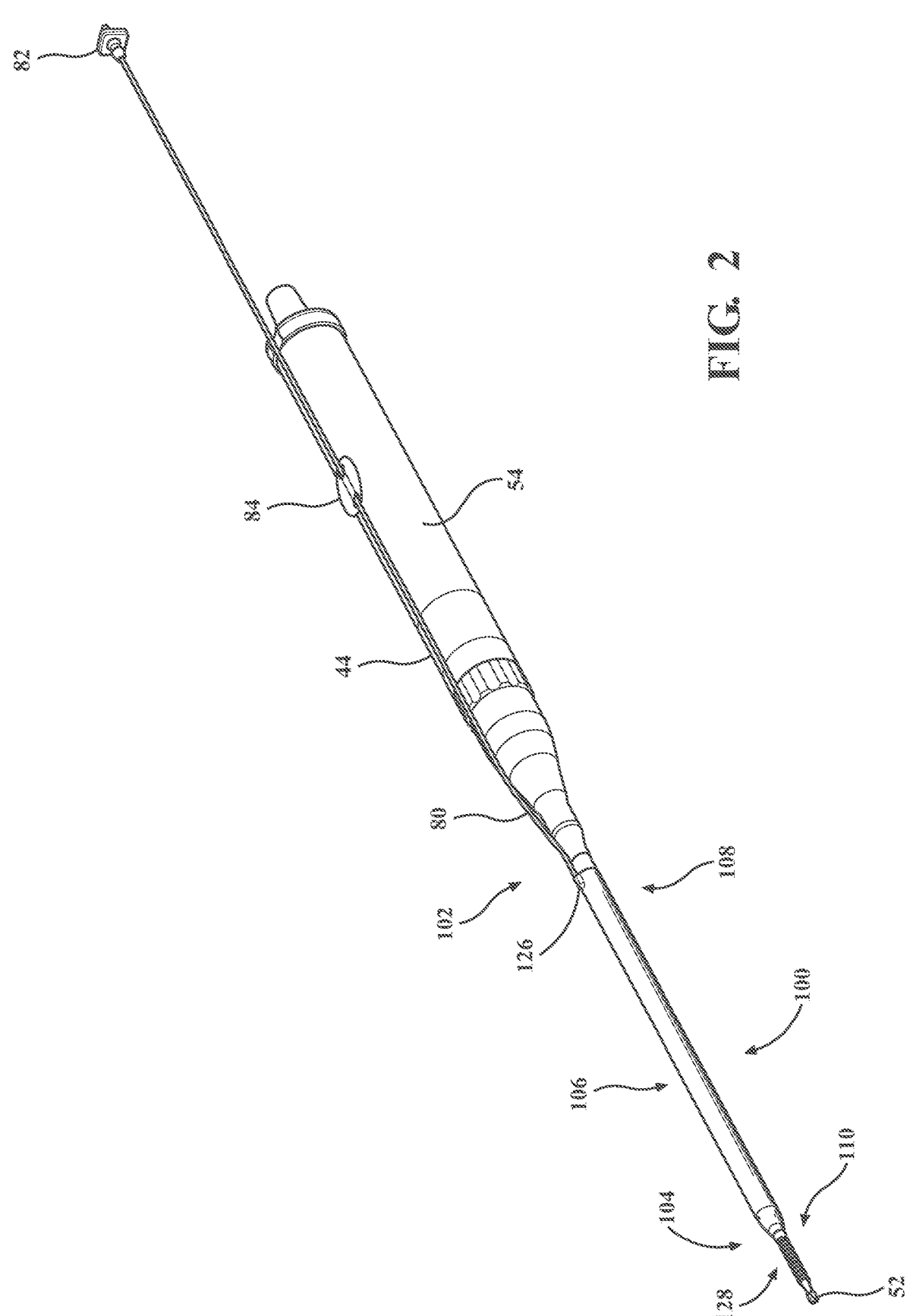
FIG. 2 is a perspective view of the rotary instrument, the cutting accessory, and the irrigation sleeve of FIG. 1.

With reference to the Figures, wherein like numerals indicate like parts throughout the several views, a surgical system 40 is shown in FIG. 1. The surgical system 40 generally comprises an irrigation system 42 and a surgical tool, each of which will be described in greater detail below. In the representative embodiment illustrated herein, the surgical tool is realized as a rotary instrument 44. A console 46 is employed to control both the irrigation system 42 and the surgical tool via a footswitch 48. However, as will be appreciated from the subsequent description below, both the irrigation system 42 and the surgical tool could be configured and controlled in a number of different ways. By way of non-limiting example, the surgical tool and the irrigation system 42 could be controlled independently, such as by discrete consoles or input devices. Suitable construction and operation of several subsystems of the surgical system 40 and irrigation system 42 are disclosed in commonly owned International Publication No. WO 2019/022791, filed on Feb. 5, 2018, the entire contents of which are hereby incorporated by reference.

The use of high-speed drills, rotating burs, open-window shavers, and the like necessarily results in the accumulation of debris at the surgical site 86. Here, the surgical system 40 employs the irrigation system 42 to direct fluid towards the surgical site 86 to loosen, float, or displace debris for subsequent removal (for example, by suction). The irrigation system 42 may also be used to ensure proper operation of surgical tools during procedures by clearing debris from endoscopes, cooling cutting accessories, preventing the accumulation of debris on cutting accessories, and the like.

Referring to FIGS. 2-5, the surgical tool is configured as the rotary instrument 44, which drives a cutting accessory, generally indicated at 52. Here, the cutting accessory 52 is adapted to assist a medical professional in approaching or manipulating a surgical site 86 by effecting the removal of tissue, bone, and the like. To this end, the cutting accessory 52 is depicted throughout the drawings as a bur. The cutting accessory 52 could be of a number of different types or configurations, such as shavers, rasps, ultrasonic cutting tools, etc. As will be discussed below, several cutting accessories 52 (see FIGS. 9-11) are available to suit the needs associated with various surgical sites 86. Specifically, different length cutting accessories 52A, 52B, 52C, i.e. those having different driveshaft lengths can be used with the rotary instrument 44. While the representative surgical tool illustrated herein is realized as a rotary instrument 44, the surgical tool could be configured in a number of different ways, including but not limited to an endoscope, a recipro-cating tool, un ultrasonic tool, and the like, from any number of components controlled in any suitable way and operable to power the cutting accessory 52.

The rotary instrument 44 generally comprises a housing 54, which supports a coupler 56 and a motor 58 therein (depicted schematically in FIG. 1). The motor 58 generates rotational torque that is translated to the coupler 56 which, in turn, is configured to releasably secure the cutting accessory 52 for concurrent rotation with the motor 58. The rotary instrument 44 further comprises a tube, generally indicated at 60, which extends from the housing 54 to a distal tube end 62. The cutting accessory 52, in turn, comprises a head 64 and a shank 66 extending from the head 64. The shank 66 is adapted to be rotatably supported by the tube 60 of the rotary instrument 44, and is secured axially to the rotary instrument 44 via the coupler 56 (not shown in detail). In the exemplary cutting accessory 52 illustrated herein, the head 64 is realized as a bur, but could be of any suitable type or configuration, as noted above.

In the exemplary rotary instrument 44 illustrated in FIG. 1, the motor 58 is powered via a wired electrical connection with the console 46 and is controlled via the footswitch 48, which is similarly disposed in electrical communication with the console 46. However, the rotary instrument 44 could be configured with or without a wired motor 58 controlled by a console 46. By way of non-limiting example, the rotary instrument 44 could be powered pneumatically or could be driven by a motor disposed within the console. Similarly, while the footswitch 48 is employed to effect control of the motor 58 via the console 46, other types of user inputs are contemplated. For example, hand switches could be operatively attached to the housing 54 of the rotary instrument 44 to control rotation of the motor 58, or the console 46 could control rotation of the motor 58 without the footswitch 48.

The irrigation system 42 of the surgical system 40 is configured to direct fluid from an irrigation source 68 towards the surgical site 86. In FIG. 1, the irrigation source 68 comprises a fluid reservoir 70 realized as a bag of saline solution disposed in fluid communication with a motor-driven pump cassette 72 which, in turn, is disposed in fluid communication with a line 74. Here, the pump cassette 72 is operatively attached to the console 46, is controlled via the footswitch 48, and is configured to direct fluid from the fluid reservoir 70 to the line 74. The line 74, in turn, is adapted to releasably attach to an irrigation sleeve assembly, generally indicated at 100, to direct fluid towards the surgical site 86 as described in greater detail below in connection with FIG. 2. An irrigation sleeve suitable for certain implementations of the irrigation system is disclosed in aforementioned commonly owned International Publication No. WO 2019/ 022791, the entire contents of which are hereby incorporated by reference.

Figure 4:
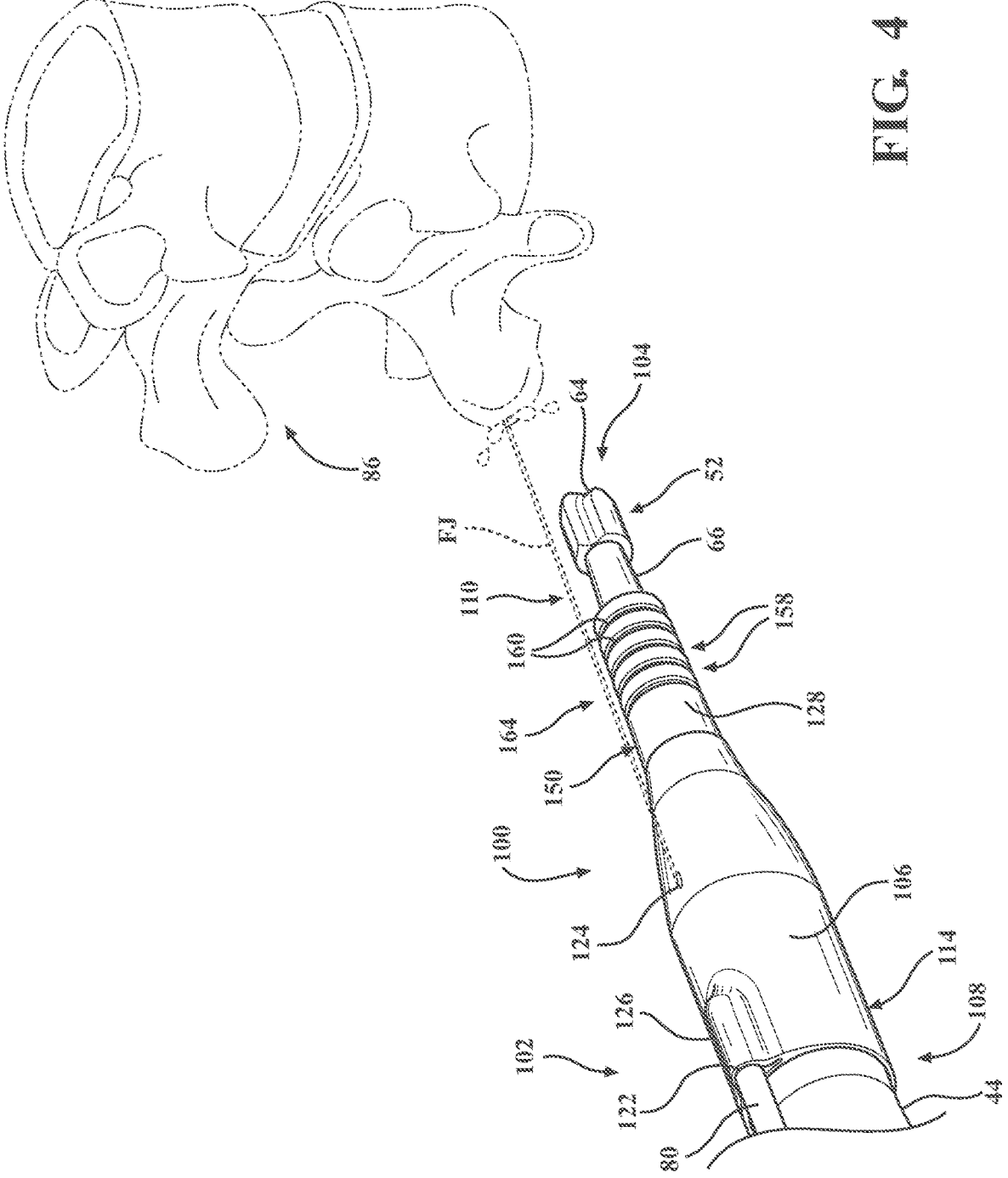
FIG. 4 is a partial perspective view of the rotary instrument, the cutting accessory, and the irrigation sleeve of FIG. 2, shown with a jet of fluid projecting next to and beyond the cutting accessory towards an illustrative surgical site comprising vertebral bone.
Figure 5:
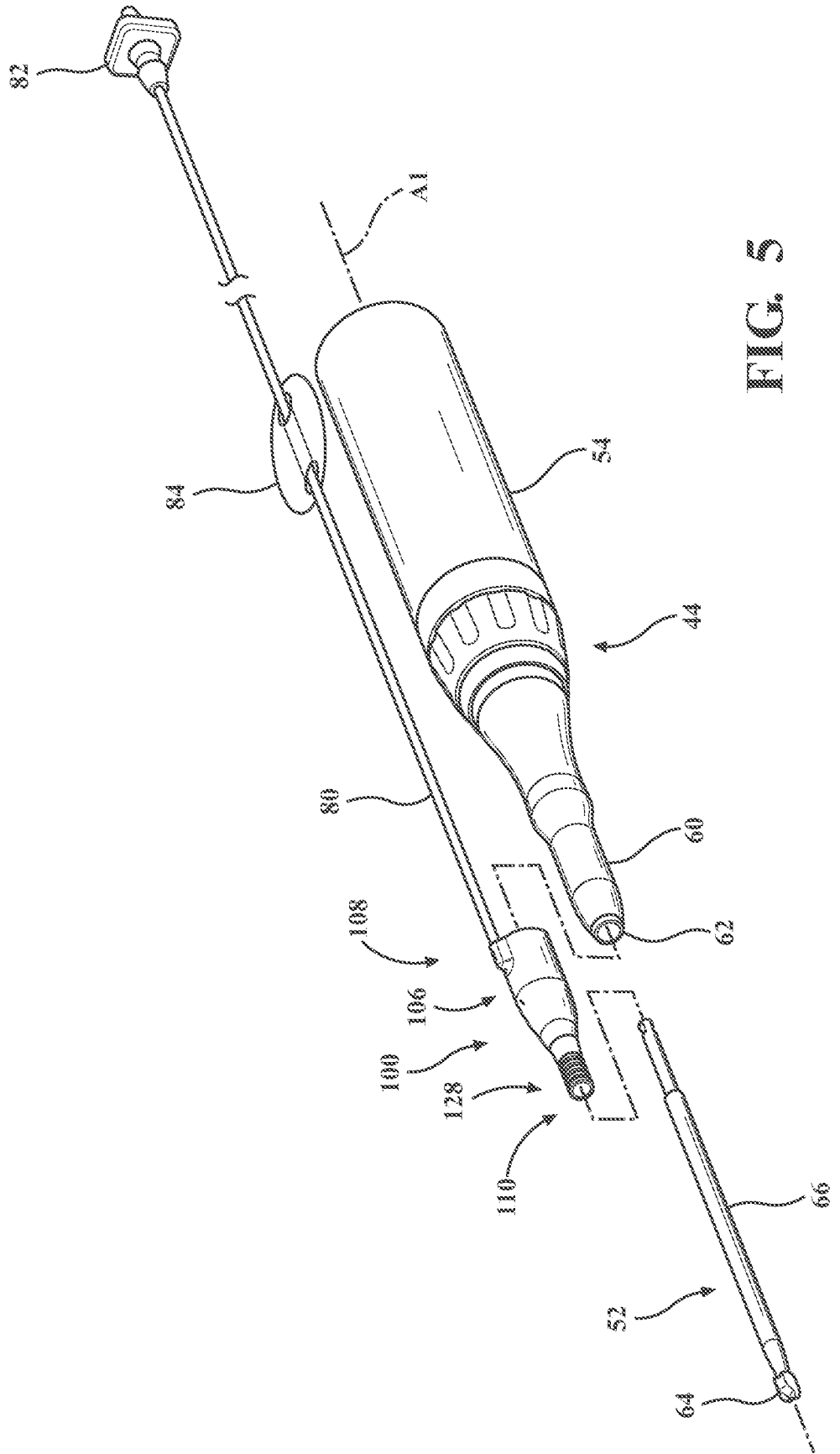
FIG. 5 is an exploded perspective view of the rotary instrument, the cutting accessory, and the irrigation sleeve of FIG. 4, the rotary instrument comprising a tube.

The irrigation sleeve 100 is adapted to be coupled to the tube 60 of the rotary instrument 44 and, in certain configurations, is configured to project a fluid jet FJ next to and beyond the head 64 of the cutting accessory 52 towards the surgical site 86 (see FIG. 4). To this end, the illustrated irrigation system 42 may further comprise a feeder tube 80, a connector 82, and an adhesive member 84. The feeder tube 80 is interposed in fluid communication between the connector 82 and the irrigation sleeve 100, and the connector 82 is adapted for attachment to the line 74 of the irrigation system 42. Thus, fluid displaced by the pump cassette 72 flows from the irrigation source 68, through the line 74 and the feeder tube 80, to the irrigation sleeve 100 which, in turn, projects the fluid jet FJ, as noted above, and as described in greater detail below.

The feeder tube 80 can be coupled to the irrigation sleeve 100 and to the connector 82 in a number of different ways, such as via ultraviolet bonding, gluing, a barbed connection, and the like. While the connector 82 is adapted for releasable attachment to the line 74 described above, other configurations are contemplated. For example, the feeder tube 80 could be of various lengths and may be adapted for attachment directly to the irrigation source 68, directly to the pump cassette 72, to a valve interface, and the like. The adhesive member 84 is coupled to the feeder tube 80 and is configured to secure the feeder tube 80 to the housing 54 of the rotary instrument 44 during use.

Conventional irrigation systems 42 can be used in connection with a number of different types of surgical tools. As such, irrigation systems 42 are generally adjustable in terms of fluid flowrate or pump speed. Thus, depending on the type of medical or surgical procedure, the specific configuration of the surgical tool being used, or the preferences of the medical professional, the irrigation system 42 may be configured to supply fluid at a particular, adjustable flowrate (for example, by selecting a certain pump speed). The irrigation systems 42 can be configured and controlled in a number of different ways. Specifically, the irrigation system 42 could be controlled via a discrete console, as noted above. Moreover, while the pump cassette 72 is advantageously driven with an electric motor via the console 46, other arrangements of irrigation sources 68 are contemplated herein. For example, displacement of fluid from the fluid reservoir 70 towards the irrigation sleeve 100 could be achieved via a manually-actuated pump. Furthermore, the irrigation system 42 and/or the surgical tool could incorporate, or otherwise cooperate with, a suction system or other systems, tools, and the like utilized in connection with medical or surgical procedures.

Furthermore, certain elements of the irrigation system 42 may be supplied individually or combined as a sub-assembly. For example, irrigation sleeve 100 may be further defined as an irrigation assembly wherein the feeder tube 80, the connector 82, and the adhesive member 84 are pre-assembled with the irrigation sleeve 100 as a single-use disposable. Alternatively, each of the components may be available as a kit to be assembled by the user. Some or all of these components may also be reusable owing to construction comprising a sterilizable material, as will be discussed in further detail below.

Referring now to FIGS. 1-19, the illustrated embodiments of the irrigation sleeve 100 are adapted to be coupled to the tube 60 of the rotary instrument 44, as noted above. The irrigation sleeve 100 has a generally elongated shape with two ends, a first end 102 and a second or working end 104, which are spaced along a longitudinal axis A1. Generally speaking, the first end 102 is arranged proximal to the user (surgeon) and the working end 104 is arranged distal to the user (surgeon). The first end 102 is configured to receive the rotary instrument 44 and the working end 104 is configured to receive the cutting accessory 52, i.e. the working end 104 is nearer to the head 64 of the cutting accessory 52, which performs the tissue removal procedure.

In one configuration, shown in FIGS. 3-8, the irrigation sleeve 100 comprises a sleeve body 106 that extends between a proximal sleeve end 108 and a distal sleeve end 110 to define a length 112. The sleeve body 106 has an outer surface 114 and an inner surface 116, and defines a generally annular profile. The inner surface 116 is accessible through a first lumen 118 formed in the proximal sleeve end 108 of the sleeve body 106. The first lumen 118 receives at least a portion of the tube 60 of the rotary instrument 44, such that the head 64 of the cutting accessory 52 is arranged at the working end 104 of the irrigation sleeve 100 when the cutting accessory 52 is installed in the rotary instrument 44. As will be appreciated from the subsequent description below, the irrigation sleeve 100 may be first positioned onto the tube 60 of the rotary instrument 44, and then the cutting accessory 52 may be subsequently secured to the rotary instrument 44. An irrigation lumen 120, spaced from the first lumen 118, is also formed in the sleeve body 106 and is isolated from the first lumen 118 such that no fluid communication occurs between the first lumen 118 and the irrigation lumen 120. Best shown in the cross-sectional view of FIG. 8, both the first lumen 118 and the irrigation lumen 120 are defined in the sleeve body 106.

Figures 6, 7:
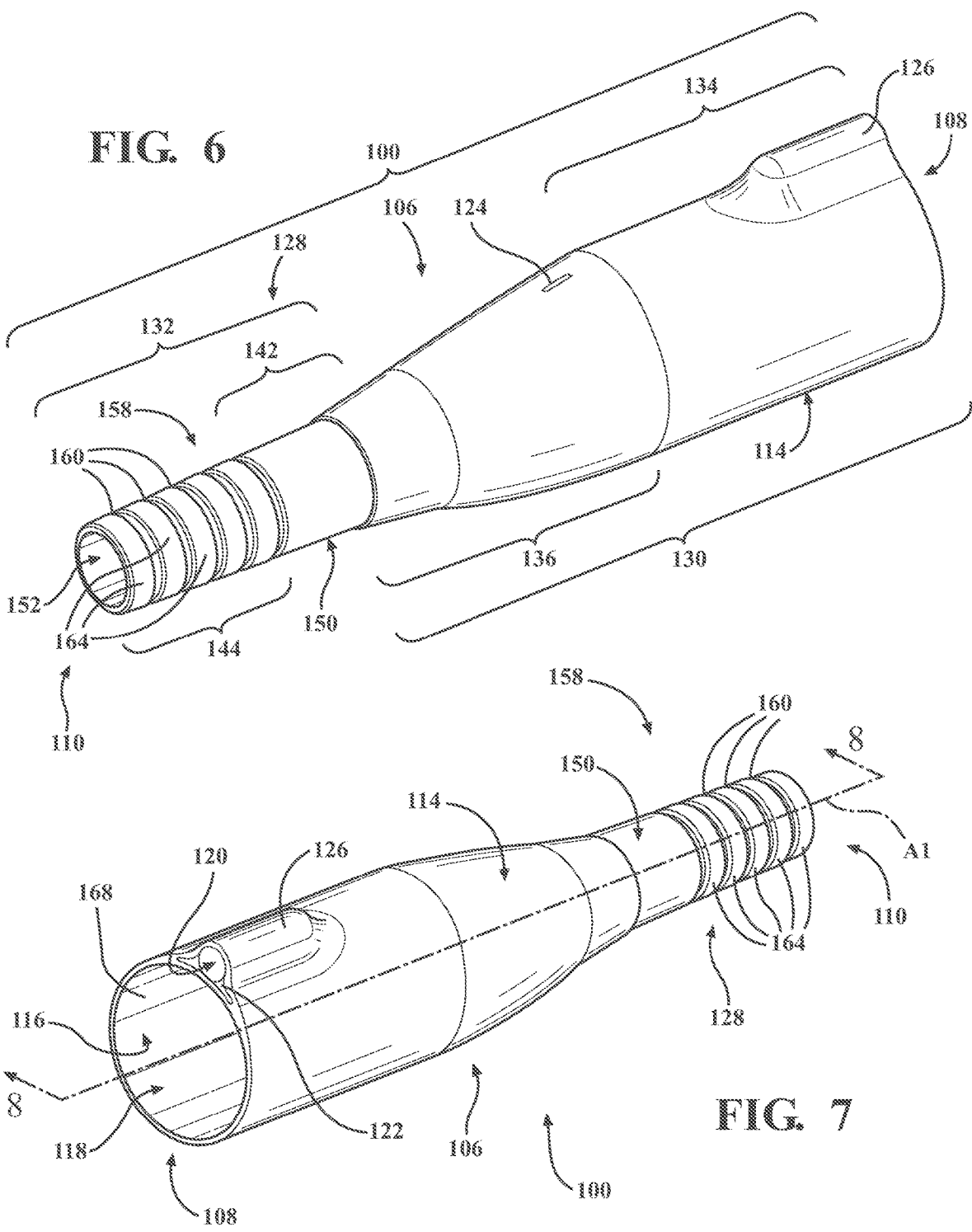
FIG. 6 is an enlarged, partial perspective view of a distal portion of the irrigation sleeve of FIGS. 3-5.
FIG. 7 is an enlarged, perspective view of a proximal portion of the irrigation sleeve of FIG. 6.

Best shown in FIGS. 6 and 7, the irrigation lumen 120 comprises an irrigation lumen inlet 122 and an irrigation lumen outlet 124. The irrigation lumen inlet 122 is adapted for fluid communication with the irrigation source 68 via the feeder tube 80 and the line 74 (see FIG. 1). The irrigation lumen inlet 122 is defined in a lumen support 126, which protrudes from the sleeve body 106 near the proximal sleeve end 108.

The irrigation lumen 120 extends from the irrigation lumen inlet 122 to the irrigation lumen outlet 124, which is defined in the sleeve body 106. The irrigation lumen outlet 124 is arranged to direct fluid adjacent to the head 64 of the cutting accessory 52. In certain configurations, the irrigation lumen outlet 124 promotes projecting the fluid jet FJ away from the shank 66 of the cutting accessory 52. In certain other configurations, the irrigation lumen outlet 124 promotes projecting the fluid jet FJ substantially parallel with the shank 66 of the cutting accessory 52. As noted above, the sleeve body 106 could have other profiles, configurations, and the like (see, for example, FIGS. 20-25)

Throughout the specification, the term irrigation sleeve 100 is used to refer to one type of instrument sleeve that is capable of providing irrigation to a location near the surgical site 86. Irrigation may be implemented into the surgical system 40 by providing an irrigation lumen 120, which may be integrated with, or separate from, the instrument sleeve so as to enable the instrument sleeve to direct fluid toward the surgical site 86. In this way, the irrigation sleeve is realized as an instrument sleeve used in combination with an irrigation lumen 120. Alternative configurations of an instrument sleeve combining aspects of the sleeve body 106 and shield extension 128 discussed herein may be realized without the irrigation lumen described above. Instrument sleeves without an irrigation lumen may be provided for use in procedures where irrigation is not used or where alternative irrigation systems 42 are used.

In certain embodiments, the irrigation sleeve 100 comprises the sleeve body 106 and may further comprise a shield extension 128 coupled to the sleeve body 106. When removing tissue with the cutting accessory 52, loose material may adhere to the shank 66 and cause tissue wrap. Specifically, when the shank 66 is spinning and contacts tissue, surface friction causes the loose tissue to adhere to the shank 66. Due to the high rotational speed of the shank 66 loose tissue that adheres to the shank 66 has a tendency to wrap around the shank 66. When the loose tissue wraps around the shank 66 tension between the loose tissue and the shank 66 increases. This increase in tension between the loose tissue and the shank 66 may continue until the shank 66 experiences adverse effects. Therefore, in order to minimize tissue wrap, unintended contact between the shank 66 and the tissue should be minimized. By decreasing the amount of the shank 66 that is exposed between the distal tube end 62 and the head 64, the shank 66 is less likely to contact loose tissue, which may bind or adhere to the shank 66. In other words, in such a configuration, there is a much smaller portion of the shank 66 that is exposed to tissue because the portion of the shank 66 that is between the head 64 and the distal tube end 62 is surrounded by the shield extension 128. This makes the shank 66, and thus the cutting accessory 52 more reliable and reduces potential trauma during use.

As used throughout the specification the terms proximal and distal refer to the arrangement of a first portion relative to a second portion of the respective element. Accordingly, the irrigation sleeve 100 has a proximal sleeve portion 130 and a distal sleeve portion 132. The proximal sleeve portion 130 is nearer to the first end 102 than the distal sleeve portion 132. Said differently, the distal sleeve portion 132 is nearer to the working end 104 than the proximal sleeve portion 130. The spatial relationships used to describe of the various elements of the irrigation sleeve 100 refer only to the configuration of their respective element. Specifically, both the sleeve body 106 and the shield extension 128 have respective proximal and distal portions, the distal portion being associated with the working end 104 and the proximal portion being associated with the first end 102 only in relation to the corresponding portion of the respective element.

More specifically, the sleeve body 106 has a proximal body portion 134 and a distal body portion 136. The proximal body portion 134 is nearer to the first end 102 than the distal body portion 136. Said differently, the distal body portion 136 is nearer to the working end 104 than the proximal body portion 134.

In the same way, the shield extension 128 has a proximal shield portion 142 and a distal shield portion 144. The proximal shield portion 142 is nearer to the first end 102 than the distal shield portion 144. Said differently, the distal shield portion 144 is nearer to the working end 104 than the proximal shield portion 142. The shield extension 128 further has an outer shield surface 150 and defines a shield lumen 152 that extends between the proximal shield portion 142 and the distal shield portion 144. The outer shield surface 150 and the shield lumen 152 cooperate to define an annular profile of the shield extension 128, the outer shield surface 150 having a shield outer diameter 154 and the shield lumen 152 having a shield lumen diameter 156, the shield outer diameter 154 being greater than the shield lumen diameter 156.

Figure 8:
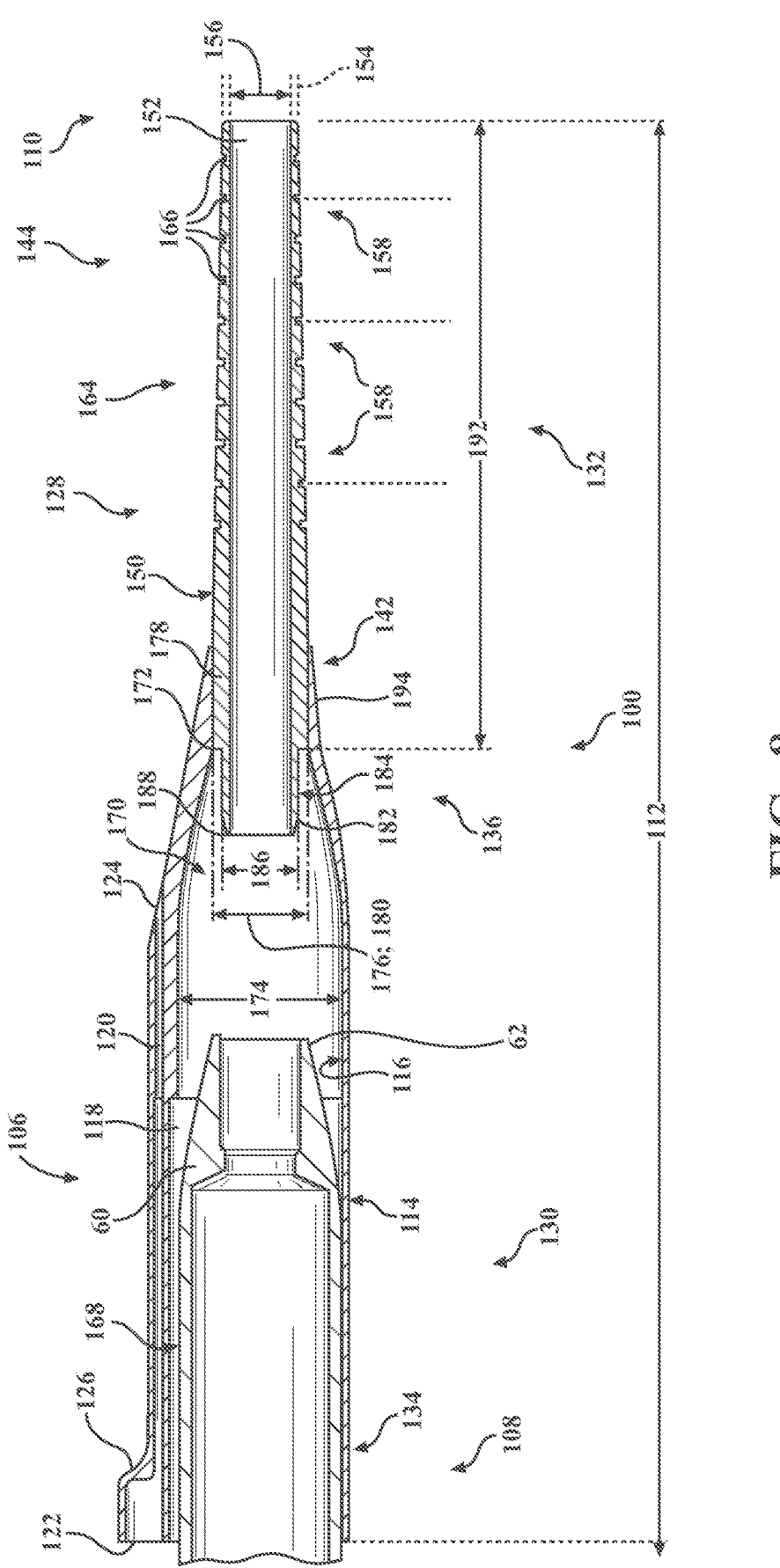
FIG. 8 is a partial section view through a vertical plane on line 8-8 in FIG. 7 showing the irrigation sleeve comprising a pilot member, the pilot member being spaced from a distal tube end of the rotary instrument tube.

As mentioned above, the shield outer diameter 154 is greater than the shield lumen diameter 156, however as can be seen in FIG. 8, the shield outer diameter 154 in the proximal shield portion 142 is greater than the shield outer diameter 154 in the distal shield portion 144. That is to say that the shield outer diameter 154 is tapered along the shield extension 128 from the proximal shield portion 142 to the distal shield portion 144. When the shield lumen diameter 156 is constant, the tapered shield outer diameter 154 has the effect of reducing a thickness of the shield extension 128 along the shield extension 128. Alternatively, it is contemplated that the shield lumen diameter 156 could increase along the shield extension from the proximal shield portion 142 to the distal shield portion 144 while the shield outer diameter 154 is constant, which would similarly reduce the thickness of the shield extension 128 nearer to the working end 104.

Cooperation between the sleeve body 106 and the shield extension 128 aligns the outer surface 114 of the sleeve body 106 adjacent to the outer shield surface 150 such that a continuous exterior surface of the irrigation sleeve 100 is formed. A length indicia 158 is arranged on the exterior surface for indicating a length of the irrigation sleeve 100. Specifically, the shield extension 128 comprises the length indicia 158, which is arranged on the outer shield surface 150 spaced at a predetermined distance from the proximal shield portion 142. The length indicia 158 may be radial scores 160 arranged along the longitudinal axis A1 concentric with the outer shield surface 150 of the shield extension 128. The radial scores 160 provide a groove that can be used to guide a scalpel or other cutting instrument for severing the shield extension at the length indicia 158.

As will be discussed in further detail below, each of the length indicia 158 indicates one or more predetermined lengths that facilitate use of different cutting accessories 52A, 52B, 52C. More specifically, a shield length 192 is defined between each of the length indicia 158 and a proximal reference 194 of the sleeve body 106. A frangible segment 164 is defined between each length indicia 158 and the distal shield portion 144 that is configured to be removed from the shield extension 128. By removing the frangible segment 164 a cutting accessory 52C having a shorter shank 66C may be engaged with the rotary instrument 44 such that the head 64C is arranged adjacent to the distal shield portion 144.

In some configurations the length indicia 158 may define a plurality of weakened segments 166, which are arranged along the distal sleeve portion 132 at predetermined intervals for facilitating customization of the length 112 of the sleeve body 106. The length 112 of the sleeve body 106 may be customized by removing at least one of the plurality of weakened segments 166 from the sleeve body 106. According to one method, the user may remove a weakened segment 166 by applying a force, which exceeds the material's strength, to a weakened segment 166, thereby causing the sleeve body 106 to break where the force is concentrated. The user may use their hands to snap the weakened segments 166 or a tool to increase the force applied.

While the length indicia 158 are illustrated throughout the various figures as radial scores 160 formed in the sleeve body 106, alternative length indicia 158 are contemplated. For example, the length indicia 158 may take the form of a ruler scale printed on the outer shield surface 150, which provides a visual reference of a distance from the distal end 62 when the irrigation sleeve 100 installed on the rotary instrument 44. The length indicia 158 may be printed using screen printing techniques, engraved using laser engraving techniques, etched via a chemical process, or applied via an adhesive label. Further, the length indicia 158 may be integrally formed with the shield extension 128 raised from the outer shield surface 150 or sunk into the outer shield surface 150. It is further contemplated that the irrigation sleeve 100 may be used in combination with a jig (not shown) having a length indicia to transfer predetermined measurements to the exterior surface in furtherance of customizing the length 112 of the irrigation sleeve 100.

The shield extension 128 may be manufactured from a polymer material in various processes known in the art. The polymer may be chosen for its specific properties, which may a thermoplastic polymer that is resilient and durable in order to resist abrasion from the cutting accessory 52 during use. In one configuration, the shield extension 128 is constructed from a polyether ether ketone (PEEK) thermoplastic polymer. Similarly, some or all of the shield extension 128 may be provided with a smooth coating to further resist abrasion. In one example, the shield lumen 152 may be provided with a slippery or low coefficient of friction coating, such as polytetrafluoroethylene. Alternatively or additionally, a biocompatible material may be deposited on the shield extension 128. In one configuration, the shield extension 128 is manufactured from a sterilizable material. In other configurations, the shield extension 128 may be manufactured from a transparent or semi-transparent material so as to promote visibility of the rotary instrument 44 during use. However, the shield extension 128 could be manufactured from any suitable material or combination or materials.

While the sleeve body 106 and the shield extension 128 are shown throughout the figures as separate components, the irrigation sleeve 100 may be realized by a unitary, one-piece construction whereby the sleeve body 106 and the shield extension 128 are formed in an integral manner. Here, the distal sleeve portion 132 is attached to the proximal sleeve portion 130 by manufacturing the irrigation sleeve 100 as a singular body with the distal sleeve portion 132 protruding from the proximal sleeve portion 130. In these realizations, the combined proximal sleeve portion 130 and the distal sleeve portion 132 each define proximal and distal sub-portions that are associated with the corresponding proximal and distal portions of either the sleeve body 106 or the shield extension 128.

Referring specifically to FIGS. 6-8, further details of the irrigation sleeve 100 are shown. The view facing the first end 102 of the irrigation sleeve 100 of FIG. 7 depicts the inner surface 116 of the sleeve body 106. The inner surface 116 is accessible through the first lumen 118 defined in the proximal sleeve end 108 for receiving at least a portion of the tube 60 of the rotary instrument 44. FIG. 8 shows the irrigation sleeve 100 slid over the tube 60 into a partially installed position. The distal tube end 62 and a portion of the tube 60 of the rotary instrument 44 have been partially inserted into the first lumen 118 such that further insertion of the tube 60 into the first lumen 118 will cause the distal tube end 62 to move toward the distal sleeve end 110 until the irrigation sleeve 100 reaches a fully installed position, shown in FIGS. 9-11.

Shown in FIG. 8, the first lumen 118 has a proximal region 168, a transition region 170, and a first lumen apex 172. The first lumen 118 extends from the proximal sleeve end 108, through the proximal region 168 and proceeds distally through the transition region 170 to the first lumen apex 172. The proximal region 168 is arranged nearest to the proximal sleeve end 108 and the transition region 170 is immediately distal to the proximal region 168. In this way, the first lumen 118 defines the inner surface 116 of the sleeve body 106, which extends between the proximal sleeve end 108 and the first lumen apex 172.

The proximal region 168 of the first lumen 118 defines a first lumen diameter 174, which is sized to accommodate the tube 60 of the rotary instrument 44. In the transition region 170 a second lumen diameter 176 is defined at the first lumen apex 172, which is smaller than the first lumen diameter 174. In order for the inner surface 116 to extend between the proximal sleeve end 108 and the first lumen apex 172, the transition region 170 of the first lumen 118 is tapered toward the first lumen apex 172 between first lumen diameter 174 and the second lumen diameter 176. Depending on the material from which the sleeve body 106 is constructed the first lumen diameter 174 may range from slightly smaller than the tube 60 to slightly larger than the tube 60. Specifically, materials that exhibit more elastic properties may be sized slightly smaller than the tube 60 such that upon assembly of the irrigation sleeve 100 and the rotary instrument 44 the sleeve body 106 is stretched, which creates a compressive force on the tube 60 thereby promoting secure attachment of the irrigation sleeve 100 to the rotary instrument 44.

The proximal shield portion 142 of the shield extension 128 further comprises a shoulder portion 178, which defines a shoulder diameter 180. The shoulder diameter 180 is less than the first lumen diameter 174 such that the shoulder portion 178 can be engaged with the distal body portion 136 of the sleeve body 106 near the first lumen apex 172. The shield extension 128 is assembled to the sleeve body 106 by inserting the shoulder portion 178 into the distal body portion 136 and the first lumen 118. To this end the shoulder diameter 180 is approximately equal to the second lumen diameter 176 such that the shoulder portion 178 is an interference fit with the sleeve body 106, which retains the shield extension 128 to the sleeve body 106.

As seen here, some configurations of the shield extension 128 may further comprise a pilot member 182 coupled to the proximal shield portion 142 and extending into the first lumen 118 in a proximal direction toward the first end 102. The pilot member 182 is configured for engagement with a portion of the tube 60 of the rotary instrument 44 to provide rigidity to the sleeve body 106. The pilot member 182 has a generally annular profile with an inner surface defined by the shield lumen 152 and a pilot surface 184, which defines a pilot diameter 186. The pilot diameter 186 is greater than the shield lumen diameter 156 and less than the first lumen diameter 174. In the embodiment illustrated herein the pilot diameter 186 is also less than the shoulder diameter 180 to provide a limit stop for engagement with the distal tube end 62. However, other configurations are contemplated where the shoulder diameter 180 and the pilot diameter 186 are equal such that the lumen apex 172 functions as the limit stop for engagement with the distal tube end 62. The shield lumen 152 extends through the pilot member 182 into communication with the first lumen 118 such that the cutting accessory 52 can be inserted into the distal sleeve end 110, through the shield lumen 152 and received by the tube 60 in the first lumen 118.

The pilot member 182 is arranged with the annular profile protruding from the shoulder portion 178, near the first lumen apex 172, into the first lumen 118 such that the pilot surface 184 extends between the first lumen apex 172 and a proximal pilot end 188. When the proximal pilot end 188 is received in the distal tube end 62 the pilot member 182 provides rigidity to the sleeve body 106 by urging the shield lumen 152 into alignment with the tube 60 of the rotary instrument 44, which constrains movement of the working end 104. In some configurations the irrigation sleeve 100 may be constructed such that the shield extension 128 does not protrude into the first lumen 118, i.e. does not have a pilot member 182.

The location of the proximal reference 194 of the sleeve body 106 may vary between different configurations of the irrigation sleeve 100. In one configuration the proximal reference 194 may be the position of the distal tube end 62 when the irrigation sleeve 100 is assembled to the rotary instrument 44 so that the shield length 192 may be determined relative to the distance that the cutting accessory 52 protrudes from the distal tube end 62. Alternatively, the proximal reference 194 may be the position of a structural element of the irrigation sleeve 100 itself, such as the lumen apex 172, the proximal pilot end 188, the shoulder portion 178, the proximal sleeve end 108, and the like.

Alignment of the tube 60 within the first lumen 118 is facilitated by the transition region 170 of the first lumen 118. When the tube 60 is inserted into the first lumen 118 the distal tube end 62 will engage the inner surface 116 of the sleeve body 106, which guides the distal tube end 62 toward the lumen apex 172 as the tube 60 is moved in a proximal to distal direction. In addition to the tapered shape of the transition region 170, the proximal pilot end 188 may be tapered near the proximal pilot end 188 to further aid in alignment of the irrigation sleeve 100 on the rotary instrument 44.

The sleeve body 106 may be manufactured from a transparent or semi-transparent material so as to promote visibility of the rotary instrument 44 during use. In one configuration, the sleeve body 106 is manufactured from a resilient, compliant, or otherwise expandable material, such as a soft plastic or rubber, to help the irrigation sleeve 100 conform to the shape of the tube 60 of the rotary instrument 44. To this end, the first lumen 118 is advantageously sized and dimensioned to closely fit over the tube 60 of the rotary instrument 44. Here, the inner surface 116 in the first lumen 118 may be provided with a non-slip or high coefficient of friction coating (for example, a co-extruded and tacky thermoplastic elastomer) to prevent inadvertent movement between the irrigation sleeve 100 and the tube 60 of the rotary instrument 44. Conversely, the outer surface 114 of the sleeve body 106 may be provided with a smooth coating (for example, polytetrafluoroethylene), or may be covered with a water-activated lubricant, to help the irrigation sleeve 100 move towards the surgical site 86. In one configuration, the sleeve body 106 is manufactured from a sterilizable material. The sleeve body 106 could be manufactured from any other suitable material or combination or materials.

In alternative or addition to the interference fit, the sleeve body 106 and the shield extension 128 may be bonded using an adhesive (not shown). The adhesive may be applied to a portion of at least one of the shoulder portion 178 and the transition region 170 of the first lumen 118 prior to insertion of the shield extension 128 into the sleeve body 106. Different types of adhesive may be utilized depending on the materials chosen for both the shield extension 128 and the sleeve body 106, for example, the adhesive may facilitate a mechanical bond by hardening to interlock each part and resist separation. Alternatively, the adhesive may facilitate a chemical bond between each part. Coupling of the sleeve body 106 and the shield extension 128 may be further accomplished by other bonding processes including, but not limited to, friction welding, ultrasonic welding, laser welding, heat staking, and the like.

In configurations where the irrigation sleeve 100 is constructed with a unitary, one-piece construction, whereby the sleeve body 106 and the shield extension 128 are formed in an integral manner, the sleeve body 106 and the shield extension 128 are formed from the same material. Here, the material chosen may be the same or similar material as described above in connection with either the sleeve body 106 of the shield extension 128. Alternatively, other materials that combine properties of either of these materials may also be used. In another configuration the irrigation sleeve 100 may be formed using a co-molding process, in which the sleeve body 106 and the shield extension 128 are integrally formed from separate materials.

Referring again to FIGS. 9-11, each figure shows different exemplary combinations of elements of the surgical system 40. Specifically, FIG. 9 shows the rotary instrument 44 fitted with a first irrigation sleeve 100A and a first cutting accessory 52A having a head 64A and a shank 66A. FIG. 10 shows the rotary instrument 44 fitted with a second irrigation sleeve 100B and a second cutting accessory 52B having a head 64B and a shank 66B. FIG. 11 shows the rotary instrument 44 fitted with a third irrigation sleeve 100C and a third cutting accessory 52C having a head 64C and a shank 66C.

As is shown in FIGS. 9-11, each of the cutting accessories 52A, 52B, 52C is different than the other and, as such, results in a different configuration of the surgical system 40. Specifically, each cutting accessory 52A, 52B, 52C has a different length shank 66A, 66B, 66C. The first shank 66A is longer than both the second shank 66B and the third shank 66C, and the second shank 66B is longer than the third shank 66C. Said differently, the first shank 66A is the longest and the third shank 66C is the shortest. The length of each shank 66A, 66B, 66C is merely intended to illustrate one of many possible configurations of cutting accessories, which may have shank lengths that are longer and shorter than are shown here. The length of the shank may be selected based on the preferences of the surgeon or the particular surgical procedure that is being performed. Because the rotary instrument 44 shown between the figures is the same, the head 64A, 64B, 64C of each cutting accessory 52A, 52B, 52C protrudes from the distal tube end 62 at a distance that corresponds with the length of the shank 66A, 66B, 66C when assembled with the rotary instrument 44.

In much the same way, the particular surgical procedure or the preferences of the surgeon may influence an exposed shank distance 190A, 190B, 190C that the head 64A, 64B, 64C of each cutting accessory 52A, 52B, 52C protrudes from the distal sleeve end 110, i.e. how much of the shank 66A, 66B, 66C is exposed outside of the irrigation sleeve 100A, 100B, 100C. The exposed shank distance 190A, 190B, 190C is a function of the length of the shank 66A, 66B, 66C and the shield length 192A, 192B, 192C. Here, the first and second irrigation sleeves 100A, 100B both have the same shield length 192A, 192B, but the first shank 66A is longer than the second shank 66B, which results in the first cutting accessory 52A having a larger exposed shank distance 190A than the exposed shank distance 190B of the second cutting accessory 52B. Similarly, the third irrigation sleeve 100C has a shorter shield length 192C than either of the first and second irrigation sleeves 100A, 100B, and the shank 66C of the third cutting accessory 52C is shorter than the shank 66A, 66B of either the first and second cutting accessories 52A, 52B. As a result, the exposed shank distance 190C of the third cutting accessory 52C is shorter than the exposed shank distance 190A, 190B of either the first and second cutting accessories 52A, 52B. Specifically, the first exposed shank distance 190A of FIG. 9 is greater than both the second exposed shank distance 190B of FIG. 10 and the third exposed shank distance 190C of FIG. 11, and the second exposed shank distance 190B is greater than the third exposed shank distance 190C. Said differently, the first exposed shank distance 190A is the longest and the third exposed shank distance 190C is the shortest.

As mentioned above, the particular surgical procedure or the preferences of the surgeon may influence the desired length of the shank 66 as well as the exposed shank distance 190. In order to encompass the greatest number of shank length and exposed shank distances the irrigation sleeve 100 can be customized to suit the preferences of the surgeon or the availability of a particular cutting accessory 52. Specifically, an irrigation sleeve 100 with a relatively long shield extension 128 is provided, which is capable of receiving a cutting accessory 52 with a shank 66 that is likewise relatively long, and providing a relatively short exposed shank distance 190. The ability of the irrigation sleeve 100 to be customized shortening the shield extension 128 affords the irrigation sleeve 100 the capability of receiving a cutting accessory 52 having a relatively short shank 66, which if used with a longer shield extension 128 would otherwise be too short to fully engage the rotary instrument 44.

Figures 12, 13:
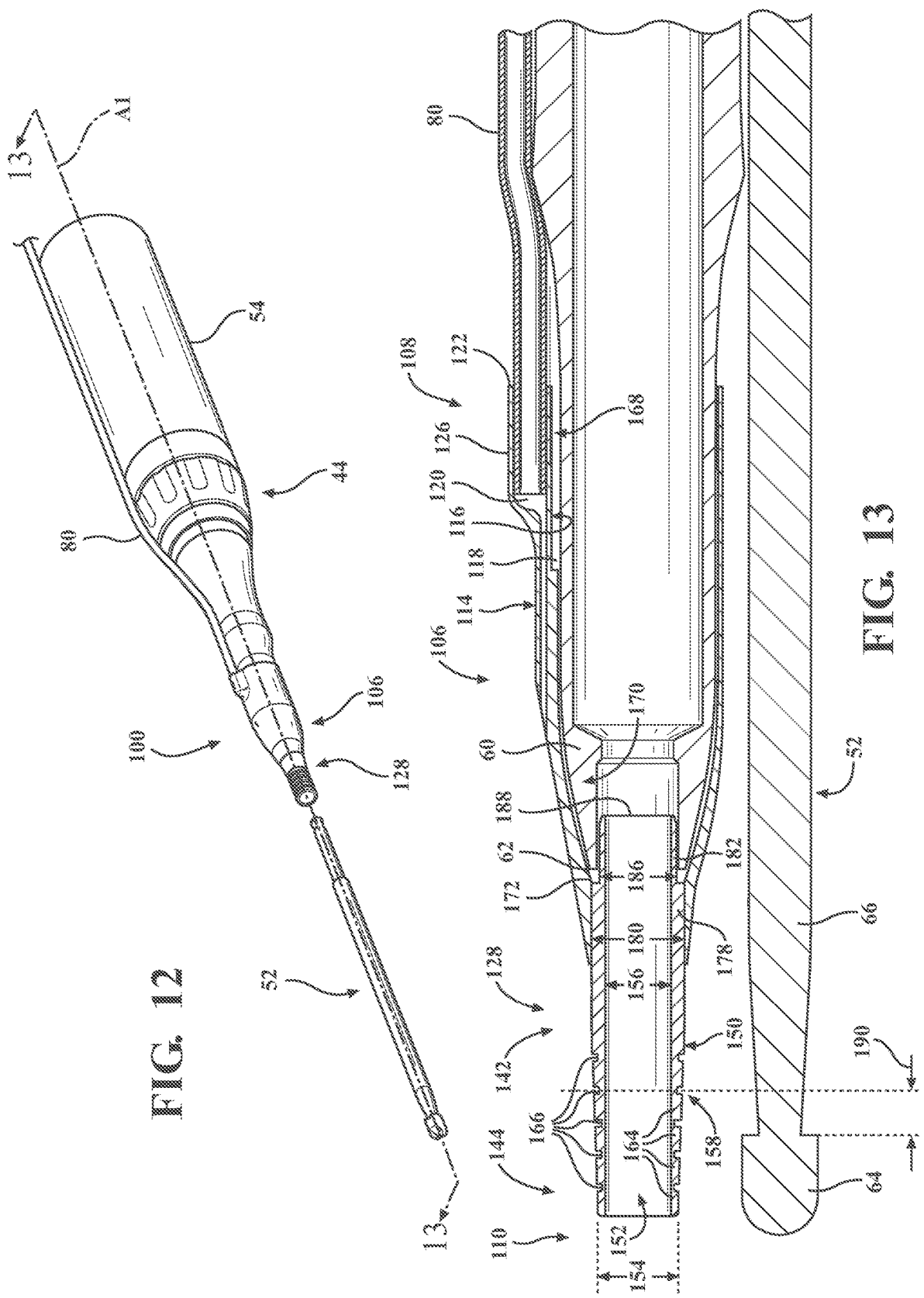
FIG. 12 is an exploded perspective view of the rotary instrument, the cutting accessory, and the irrigation sleeve of FIG. 5, shown with the irrigation sleeve assembled on the rotary instrument.
FIG. 13 is a partial section view through a vertical plane on line 13-13 of FIG. 12 showing the rotary instrument, the cutting accessory, and the irrigation sleeve and showing a severing line.

A method for customizing a surgical system 40 in connection with the irrigation sleeve 100 is provided. In FIG. 12, the rotary instrument 44 having the tube extending to a distal tube end 62 is shown. The cutting accessory 52 is shown disengaged and spaced from both the irrigation sleeve 100 and the rotary instrument 44 along the longitudinal axis A1. The method comprises a step of providing the irrigation sleeve 100 having the sleeve body 106, the lumen 118 formed in the sleeve body 106, and the shield extension 128 having at least one length indicia 158 coupled to the sleeve body 106.

The method further includes a step of coupling the irrigation sleeve 100 to the rotary instrument 44 such that at least a portion of the tube 60 is disposed in the lumen 118. The irrigation sleeve 100 is slid over the tube 60 until the pilot member 182 is received in the distal tube end 62. In this embodiment the irrigation sleeve 100 is provided separately from the rotary instrument 44. Alternatively, the irrigation sleeve 100 may be provided installed on the rotary instrument 44, as will be discussed in further detail below. In this step the method may further comprise a step of fluidly coupling the irrigation lumen 120 to the irrigation source 68. Fluidly coupling the irrigation lumen 120 to the irrigation source 68 may be accomplished by coupling the feeder tube 80 to the line 74 via the connector, by inserting the feeder tube 80 into the irrigation lumen inlet 122, by coupling a pre-assembled feeder tube 80 directly to the pump cassette 72, and the like.

In FIG. 13, a close-up section view of the rotary instrument 44 with the irrigation sleeve 100 installed and the cutting accessory 52 spaced beneath the rotary instrument 44 in a position that corresponds to a fully installed position of the cutting accessory 52. Here, in this view the shield length 192 is shown relative to the exposed shank distance 190 that would result from assembly of this surgical system 40. It can be seen that the head 64 would limit insertion of the cutting accessory 52 into the tube 60. Said differently, the shank 66 of the cutting accessory 52 is too short to fully engage the rotary instrument 44 due to interference between the head 64 and the shield extension 128.

Figure 14:
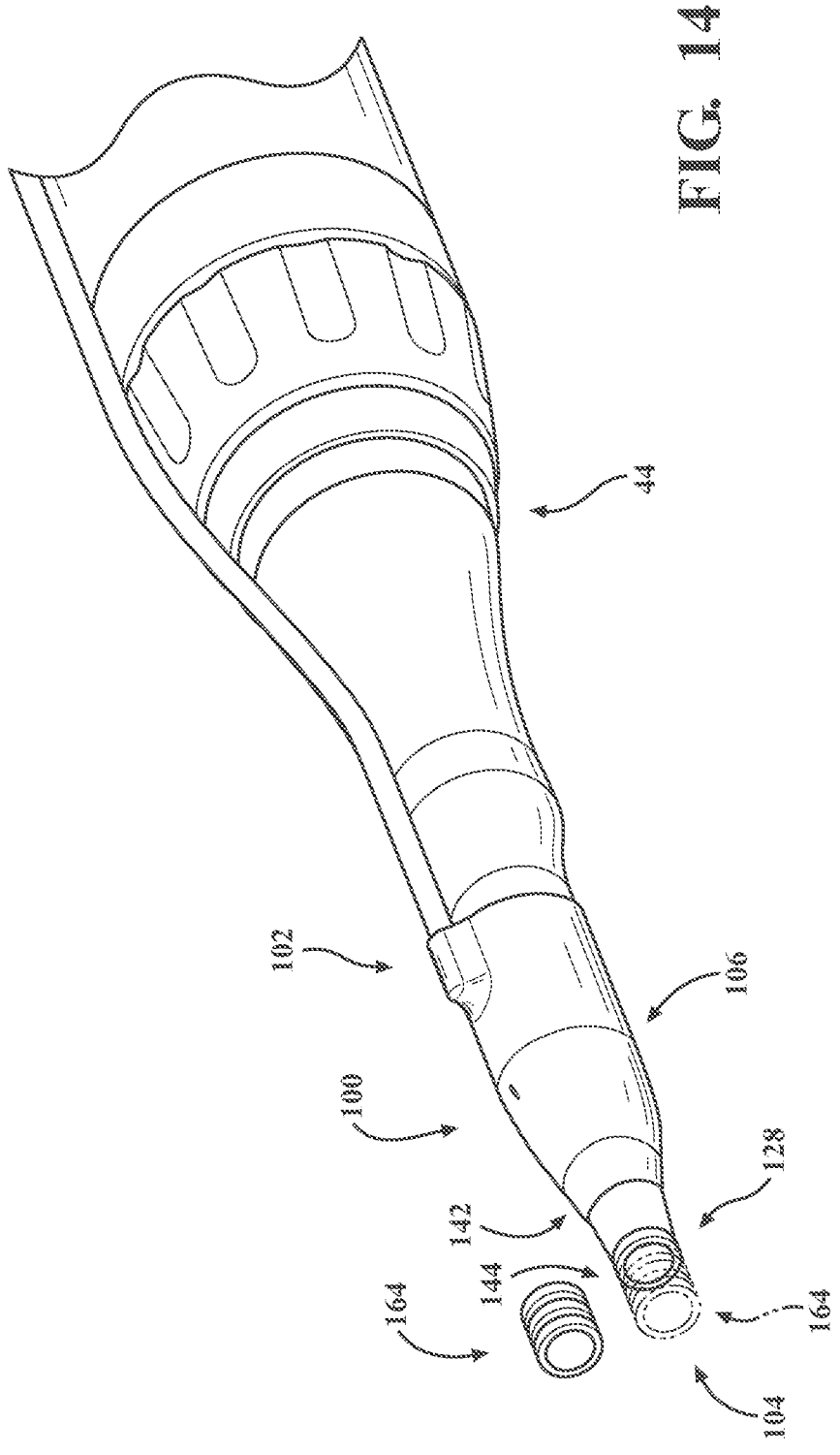
FIG. 14 is a partial perspective view of the rotary instrument and the irrigation sleeve of FIGS. 12 and 13, shown with a distal portion of the irrigation sleeve in a pre- and post-removed position.

In order to assemble the surgical system 40, the method further comprises a step of severing the shield extension 128 at one of the at least one length indicia 158, as shown in FIG. 14. Here, one of the frangible segments 164 has been removed from the distal shield portion 144 and is spaced from the irrigation sleeve 100. The frangible segment 164 is shown in phantom prior to the step of severing the shield extension 128.

An alternative method for customizing the surgical system 40 in connection with the irrigation sleeve 100 is also provided. The method comprises a step of providing the irrigation sleeve 100 comprising the sleeve body 106 having a plurality of weakened segments 166, the lumen 118 formed in the sleeve body 106, and the pilot member 182 disposed in the first lumen 118. The method further comprises a step of sliding the sleeve body 106 over the rotary instrument 44 such that the tube 60 is received by the lumen 118. A step of engaging the pilot member 182 with the distal tube end 62 ensures that the irrigation sleeve 100 is fully engaged with the tube 60.

Best shown in FIG. 13, the method further comprises a step of removing at least one of the weakened segments 166 from the sleeve body 106 such that when the cutting accessory 52 is rotatably supported by the tube 60 of the rotary instrument 44 the shank 66 engages the rotary instrument 44 and the head 64 is spaced from the lumen 118. As mentioned above, the irrigation sleeve may be supplied installed on the rotary instrument 44 prior to removing one of the weakened segments 166. In this way the step of providing the irrigation sleeve 100 and the step of sliding the sleeve body 106 over the rotary instrument 44 are combined to be performed prior to severing the shield extension 128. However, in the event that the irrigation sleeve 100 is supplied separately from the rotary instrument 44 it should be appreciated that the step of inserting the tube 60 of the rotary instrument 44 into the lumen 118 can be performed before, as well as after, a step of severing the shield extension 128 using the weakened segments 166 at one of the length indicia 158 in order to remove one of the frangible segments 164.

Best shown in FIGS. 15 and 16, the method further comprises a step of and inserting the cutting accessory 52 through the lumen 118 and engaging the shank 66 with the rotary instrument 44. In FIG. 15 a close up section view of the cutting accessory 52 inserted through the lumen 118 with the head 64 arranged adjacent to the distal shield portion 144 is shown. The weakened segment 176 has been removed from the distal shield portion 144 and is spaced from the irrigation sleeve 100 showing where the head 64 of the cutting accessory 52 would otherwise interfere with the irrigation sleeve 100.

Figure 3:
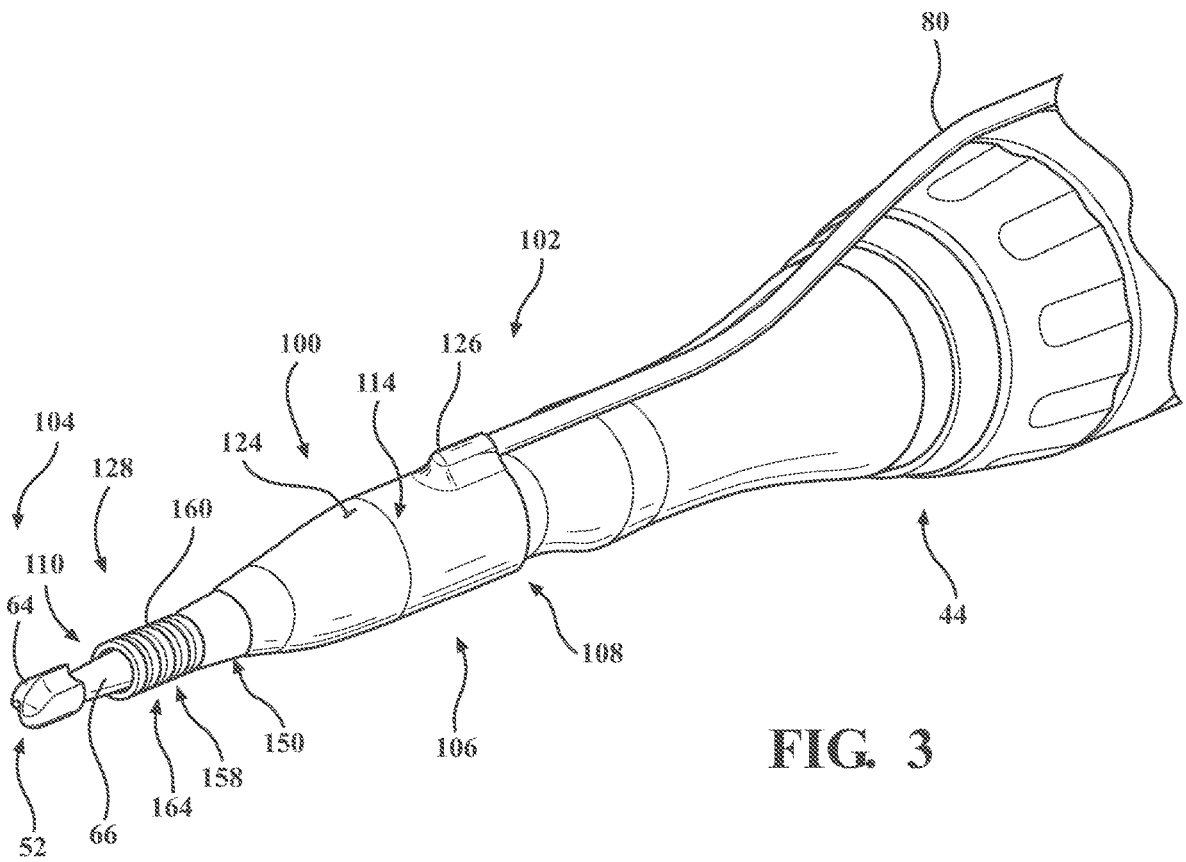
FIG. 3 is an enlarged perspective view of the rotary instrument, the cutting accessory, and the irrigation sleeve according to one embodiment.
Figures 17, 18:
FIG. 17 is a partial perspective view of the distal portion of the irrigation sleeve and the cutting accessory, according to another embodiment.
FIG. 18 is a perspective view of the proximal portion of the irrigation sleeve of FIG. 17.

Referring now to FIGS. 3 and 17, an alternative embodiment of the surgical system 40 is shown. This embodiment is similar to the first embodiment of the surgical system 40 described above in connection with FIGS. 4-16. As such, the components and structural features of this embodiment of the surgical system 40 that are the same as or that otherwise correspond to the first embodiment of the surgical system 40 are provided with the same reference numerals. While the specific differences between these embodiments will be described in detail, for the purposes of clarity and consistency, only certain structural features and components common between these embodiments will be discussed and depicted in the drawing(s) of the second embodiment of the surgical system 40. Here, unless otherwise indicated, the above description of the first embodiment of the surgical system 40 may be incorporated by reference with respect to the second embodiment of the surgical system 40 without limitation. With this background in mind, the surgical system 40 comprises the rotary instrument 44, the cutting accessory 52, and the irrigation sleeve 100, which is installed on the rotary instrument 44. In comparison to the rotary instrument 44 shown in FIGS. 2 and 4-16, the rotary instrument of FIGS. 3 and 17 comprises a tube 60 that is longer.

Figure 19:
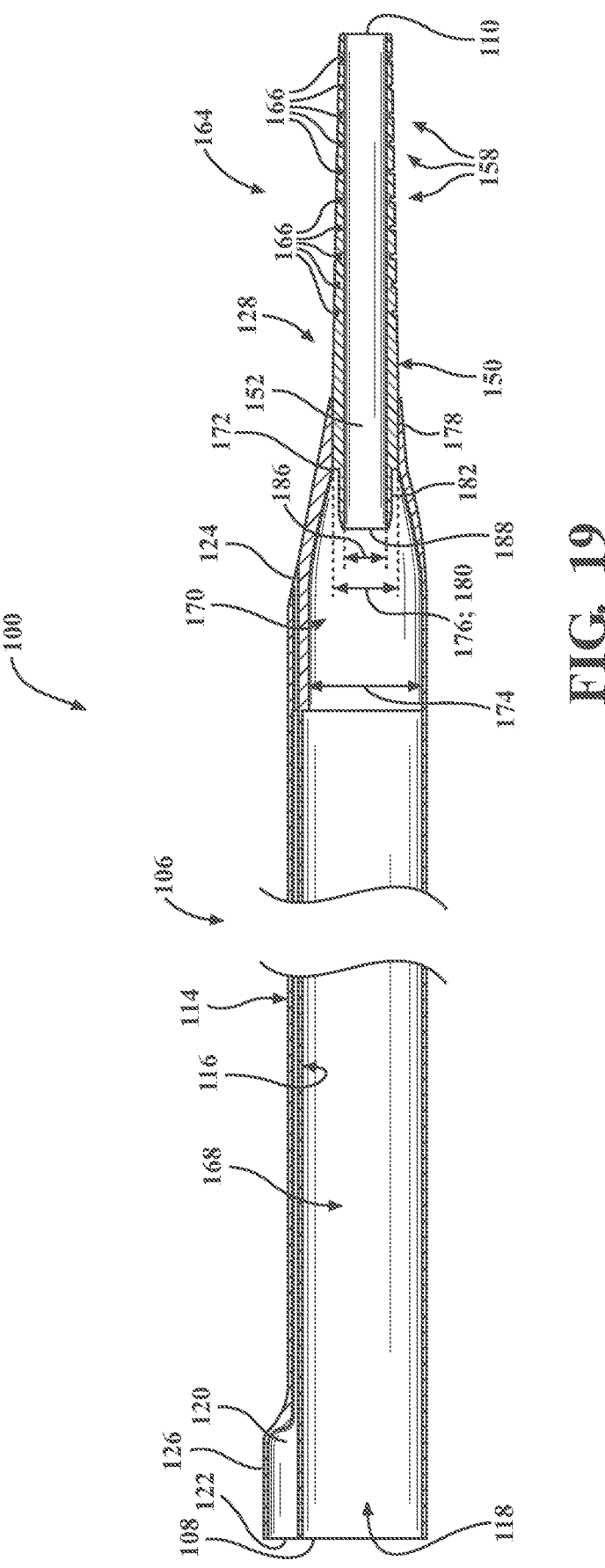
FIG. 19 is a split section-view through a vertical plane on line 19-19 of FIG. 18 showing the irrigation sleeve of FIGS. 17 and 18.

The irrigation sleeve 100 according to this embodiment is shown removed from the rotary instrument 44 and the cutting accessory 52 in FIGS. 18 and 19. Here both the first end 102 and the working end 104 of the irrigation sleeve 100 can be seen, showing the increased length of the sleeve body 106. The increased length of the sleeve body 106 allows the first lumen 118 to be correspondingly increased in size to accommodate the longer tube 60. It should be appreciated that different lengths of the proximal sleeve portion 130 and the distal sleeve portion 132 can be provided to suit different rotary instruments 44 within the scope of the present disclosure. Likewise, the lengths of the shield extension 128 and to the sleeve body 106 can be supplied in standard increments to facilitate customization of the irrigation sleeve 100 to lengths falling between each standard increment.

Figures 20, 21:
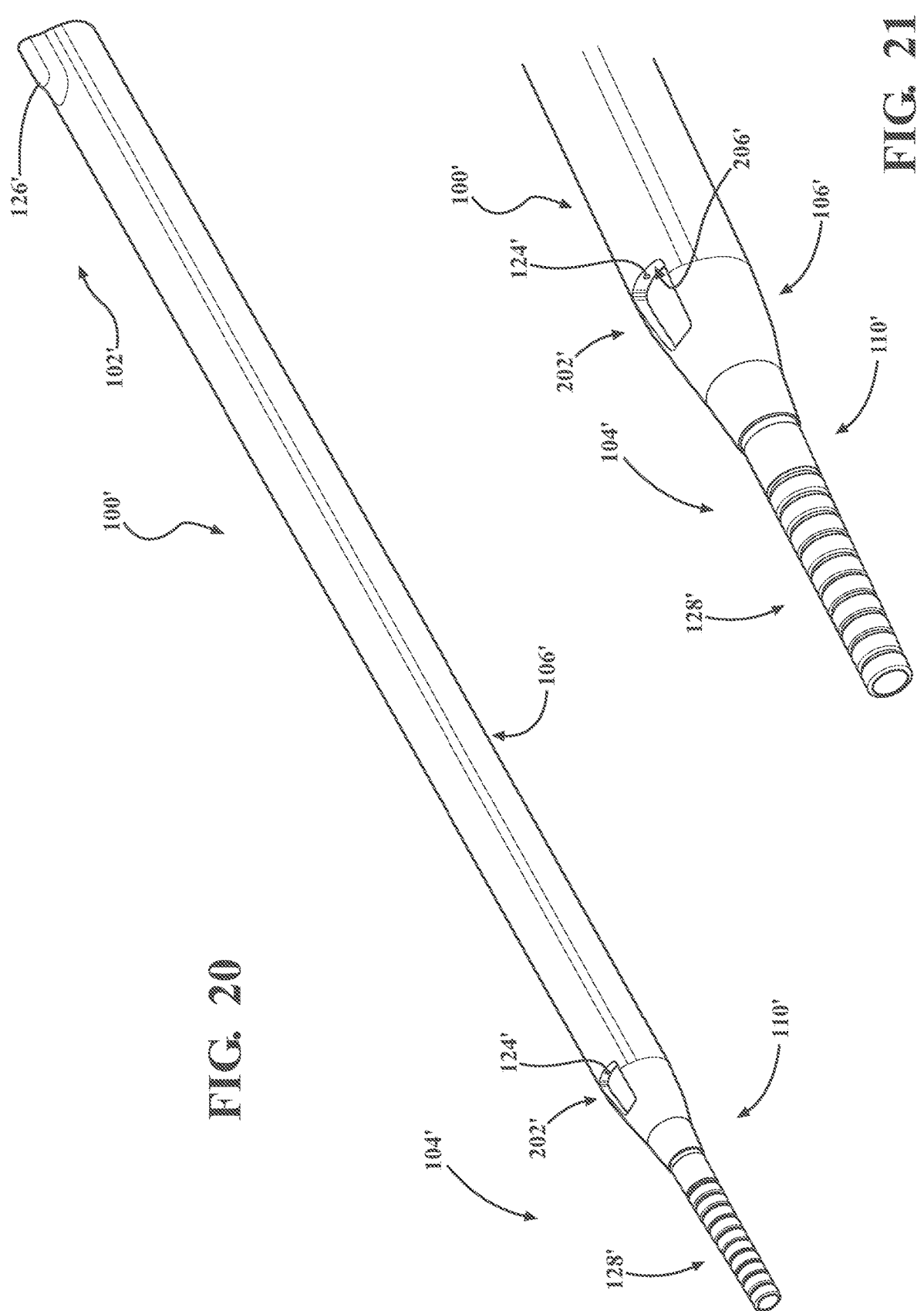
FIG. 20 is a perspective view of another embodiment of the irrigation sleeve shown with a punched feature defined in a distal body portion.
FIG. 21 is an enlarged, partial perspective view of a distal end of the irrigation sleeve with the punched feature of FIG. 20.
Figures 22, 25:
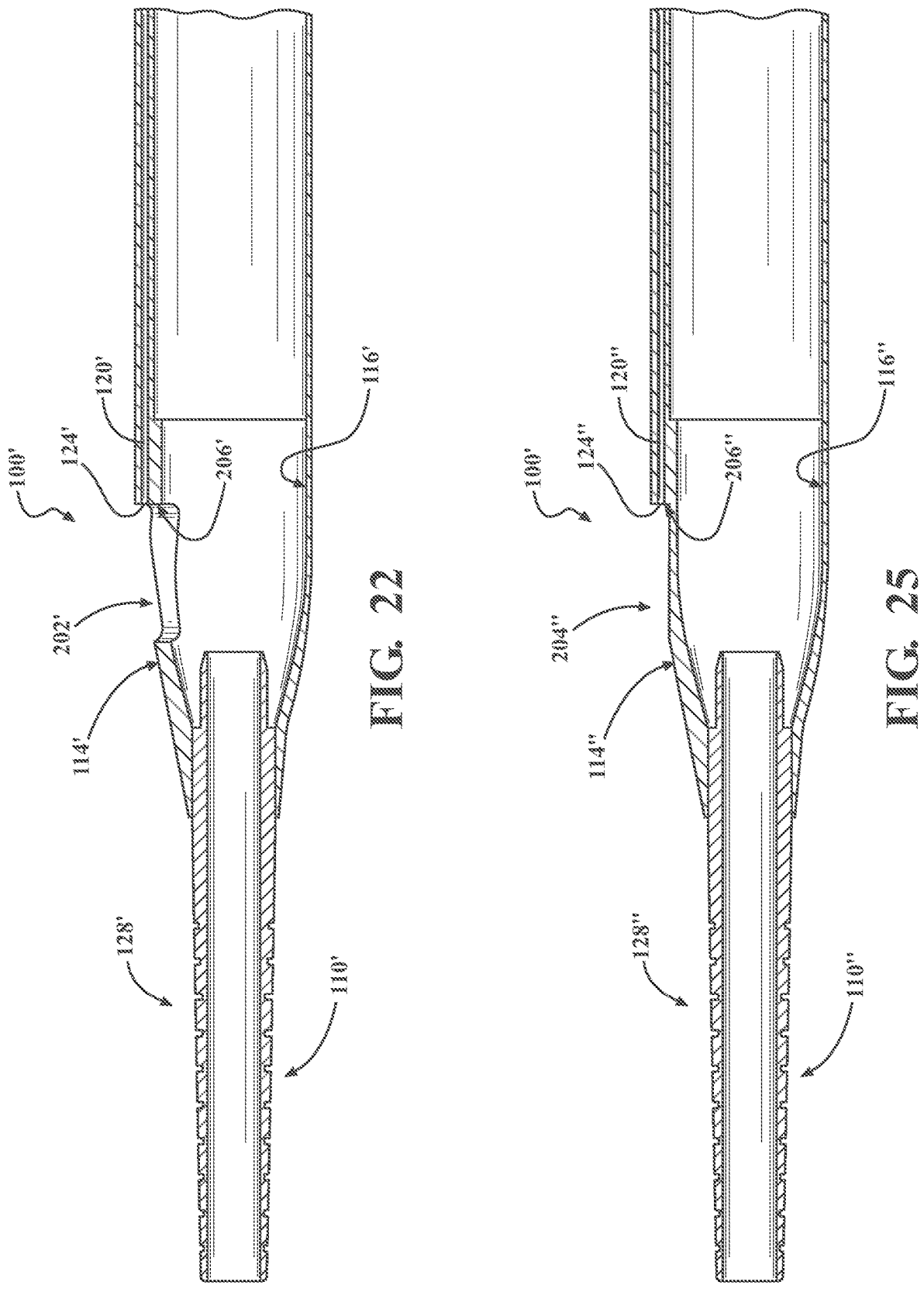
FIG. 22 is a cross-sectional view taken along line 22-22 in FIG. 21 of the distal end of the irrigation sleeve with the punched feature.
FIG. 25 is a cross-sectional view taken along line 25-25 in FIG. 24 of the distal end of the irrigation sleeve with the skived feature.
Figures 23, 24:
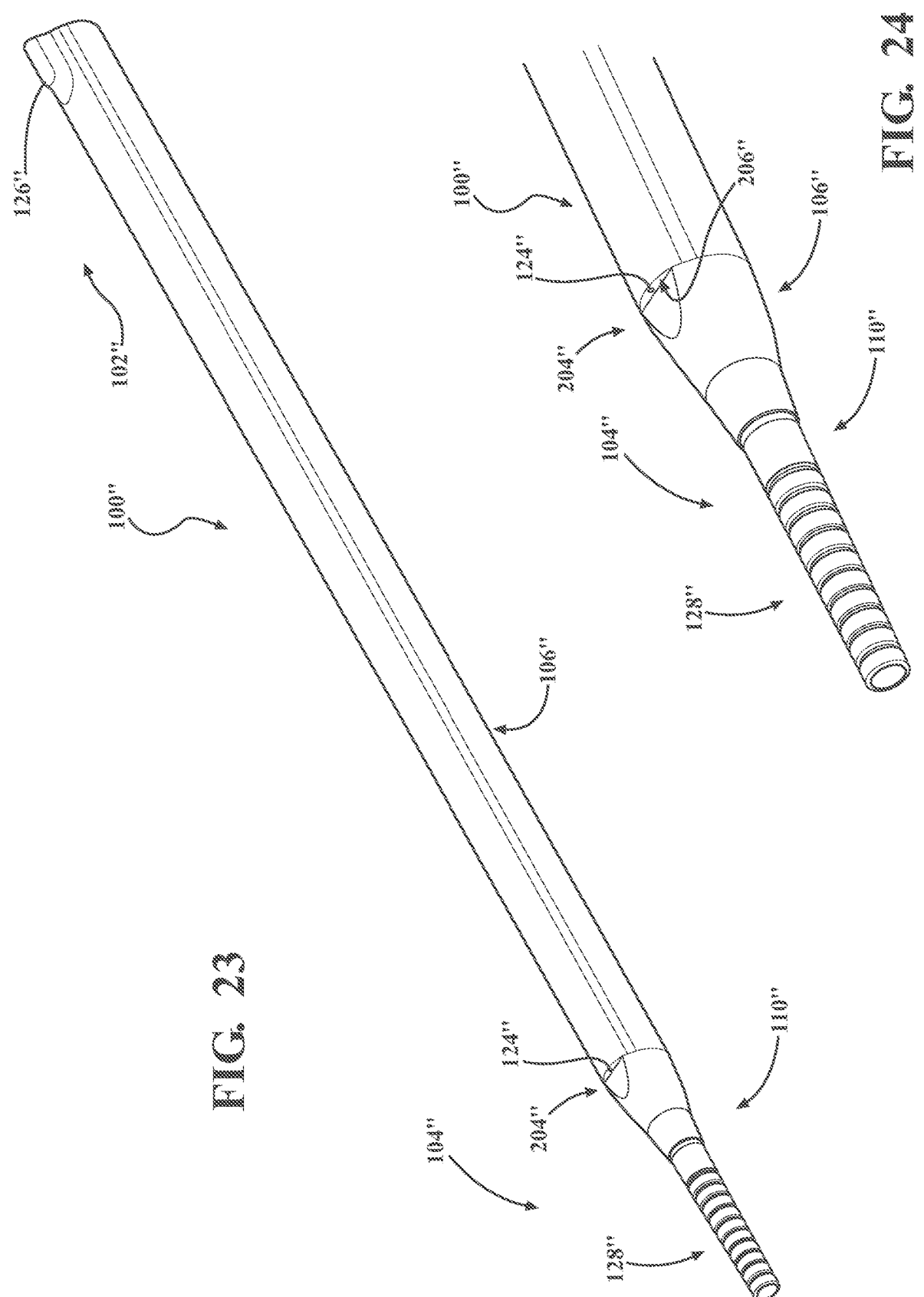
FIG. 23 is a perspective view of another embodiment of the irrigation sleeve shown with a skived feature defined in a distal body portion.
FIG. 24 is an enlarged, partial perspective view of a distal end of the irrigation sleeve with the skived feature of FIG. 23.

FIGS. 20-25 show two alternative implementations of the irrigation lumen of the irrigation sleeve. In many respects, the irrigation sleeve 100', 100" may be similar to that previously described with like numerals (plus a prime or double prim symbol e.g. 100' and 100") corresponding to like components, and any disclosure common to the corresponding components may be considered omitted in the interest of brevity should not be construed as limiting. Specifically, FIGS. 20-22 show a punched feature 202' and FIGS. 23-25 show a skived feature 204".

As shown in FIG. 22, the punched feature 202' is arranged near the distal sleeve end 110' of the sleeve body 106' and extends through the sleeve body 106' from the outer surface 114' to the inner surface 116'. The punched feature 202' defines an outlet surface 206' and the lumen outlet 124', with the lumen outlet 124' arranged on the outlet surface 206'. The outlet surface 206' is generally perpendicular to the fluid jet FJ (see FIG. 4) such that fluid is directed out of the lumen outlet 124' toward the desired location. The fluid jet FJ may be approximately parallel to the longitudinal axis A1 (see FIG. 18) extending through the sleeve body 106', as the case may be.

Similar to above and as shown in FIG. 25, the skived feature 204" is arranged near the distal sleeve end 110" of the sleeve body 106" and modifies the outer surface 114" of the sleeve body 106" by locally reducing a thickness of the sleeve body 106" such that the outlet surface 206" is defined adjacent to the outer surface 114". The outlet surface 206" is generally perpendicular to the fluid jet FJ (see FIG. 4) such that fluid is directed out of the lumen outlet 124" toward the desired location. The fluid jet FJ may be approximately parallel to the longitudinal axis A1 (see FIG. 18) extending through the sleeve body 106', as the case may be.

As discussed above, the term irrigation sleeve 100 refers to one type of instrument sleeve, which is capable of providing irrigation to a location near the surgical site. It should be appreciated that the term irrigation sleeve may also be used to refer to an instrument sleeve without the irrigation lumen described above.

Several examples have been discussed in the foregoing description. However, the examples discussed herein are not intended to be exhaustive or limit the invention to any particular form. The terminology that has been used is intended to be in the nature of words of description rather than of limitation. Many modifications and variations are possible in light of the above teachings and the invention may be practiced otherwise than as specifically described.

What is claimed is:

1. An irrigation sleeve for use with a surgical system comprising an irrigation source, a rotary instrument having a tube extending to a distal tube end, and a cutting accessory having a head and a shank adapted to be rotatably supported by the tube of the rotary instrument, the irrigation sleeve comprising:

a sleeve body extending between a proximal body portion and a distal body portion;

a first lumen formed in said sleeve body for receiving at least a portion of the tube of the rotary instrument;

a second lumen formed in said sleeve body and spaced out of fluid communication with said first lumen;

a shield extension coupled to said sleeve body and having a proximal shield portion and a distal shield portion, said proximal shield portion engaged with said distal body portion, said shield extension adapted to minimize tissue wrap about the cutting accessory shank; and a third lumen formed in said shield extension and in communication with said first lumen;

wherein said shield extension further comprises a pilot member coupled to said proximal shield portion and at least partially disposed in said first lumen; and wherein said first lumen defines a first lumen diameter, said third lumen defines a third lumen diameter, and said pilot member defines a pilot diameter, said pilot diameter being greater than said third lumen diameter and less than said first lumen diameter.

2. The irrigation sleeve as set forth in claim 1, wherein said shield extension further comprises a shoulder portion adjacent to said pilot member, said shoulder portion defining a shoulder diameter greater than said pilot diameter and less than said first lumen diameter.

3. The irrigation sleeve as set forth in claim 2, wherein said shield extension further comprises a tapered portion arranged between said shoulder portion and said distal shield portion.

4. The irrigation sleeve as set forth in claim 3, wherein said tapered portion comprises an outer surface having a length indicia arranged a predetermined distance from said proximal shield portion for indicating a distance between said length indicia and said proximal shield portion.

5. The irrigation sleeve as set forth in claim 4, wherein said length indicia comprises a radial score in said outer surface.

6. The irrigation sleeve as set forth in claim 4, wherein a frangible segment is defined between said length indicia and said distal shield portion, wherein said frangible segment is configured to be removed from said shield extension such that the head of a cutting accessory having a shorter shank may be arranged adjacent to said distal shield portion.

7. The irrigation sleeve as set forth in claim 1, wherein said shield extension is constructed from a PEEK material.

8. An irrigation sleeve for use with a surgical system comprising an irrigation source, a rotary instrument having a tube extending to a distal tube end, and a cutting accessory having a head and a shank adapted to be rotatably supported by the tube of the rotary instrument, the irrigation sleeve comprising:

a sleeve body extending between a proximal body portion and a distal body portion;

a first lumen formed in said sleeve body for receiving at least a portion of the tube of the rotary instrument;

a second lumen formed in said sleeve body and spaced out of fluid communication with said first lumen;

a shield extension coupled to said sleeve body and having a proximal shield portion and a distal shield portion, said proximal shield portion engaged with said distal body portion, said shield extension adapted to minimize tissue wrap about the cutting accessory shank; and a third lumen formed in said shield extension and in communication with said first lumen;

wherein said shield extension is bonded to said sleeve body by an adhesive.

9. The irrigation sleeve as set forth in claim 8, wherein said shield extension further comprises a pilot member coupled to said proximal shield portion and at least partially disposed in said first lumen.

10. The irrigation sleeve as set forth in claim 9, wherein said first lumen defines a first lumen diameter, said third lumen defines a third lumen diameter, and said pilot member defines a pilot diameter, said pilot diameter being greater than said third lumen diameter and less than said first lumen diameter.

11. The irrigation sleeve as set forth in claim 10, wherein said shield extension further comprises a shoulder portion adjacent to said pilot member, said shoulder portion defining a shoulder diameter greater than said pilot diameter and less than said first lumen diameter.

12. The irrigation sleeve as set forth in claim 11, wherein said shield extension further comprises a tapered portion arranged between said shoulder portion and said distal shield portion.

13. An irrigation sleeve for use with a surgical system comprising an irrigation source, a rotary instrument having a tube extending to a distal tube end, and a cutting accessory having a head and a shank adapted to be rotatably supported by the tube of the rotary instrument, the irrigation sleeve comprising:

a sleeve body extending between a proximal body portion and a distal body portion;

a first lumen formed in said sleeve body for receiving at least a portion of the tube of the rotary instrument;

a second lumen formed in said sleeve body and spaced out of fluid communication with said first lumen;

a shield extension coupled to said sleeve body and having a proximal shield portion and a distal shield portion, said proximal shield portion engaged with said distal body portion, said shield extension adapted to minimize tissue wrap about the cutting accessory shank; and a third lumen formed in said shield extension and in communication with said first lumen;

wherein said proximal shield portion defines a proximal shield portion diameter and said distal shield portion defines a distal shield portion diameter, said distal shield portion diameter less than said proximal shield portion diameter.

14. The irrigation sleeve as set forth in claim 13, wherein said shield extension further comprises a pilot member coupled to said proximal shield portion and at least partially disposed in said first lumen.

15. The irrigation sleeve as set forth in claim 14, wherein said first lumen defines a first lumen diameter, said third lumen defines a third lumen diameter, and said pilot member defines a pilot diameter, said pilot diameter being greater than said third lumen diameter and less than said first lumen diameter.

16. The irrigation sleeve as set forth in claim 15, wherein said shield extension further comprises a shoulder portion adjacent to said pilot member, said shoulder portion defining a shoulder diameter greater than said pilot diameter and less than said first lumen diameter.

17. The irrigation sleeve as set forth in claim 16, wherein said shield extension further comprises a tapered portion arranged between said shoulder portion and said distal shield portion.

\* \* \* \* \*